(12) United States Patent
Prakash et al.

(10) Patent No.: US 8,278,425 B2
(45) Date of Patent: Oct. 2, 2012

(54) N-SUBSTITUTED-AMINOMETHYLENE BRIDGED BICYCLIC NUCLEIC ACID ANALOGS

(75) Inventors: Thazha P. Prakash, Carlsbad, CA (US); Balkrishin Bhat, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 275 days.

(21) Appl. No.: 12/602,074

(22) PCT Filed: May 22, 2008

(86) PCT No.: PCT/US2008/064591
§ 371 (c)(1),
(2), (4) Date: Jun. 10, 2010

(87) PCT Pub. No.: WO2008/150729
PCT Pub. Date: Dec. 11, 2008

(65) Prior Publication Data
US 2010/0249211 A1 Sep. 30, 2010

Related U.S. Application Data

(60) Provisional application No. 60/940,835, filed on May 30, 2007.

(51) Int. Cl.
*C07H 19/00* (2006.01)
*C07H 21/04* (2006.01)

(52) U.S. Cl. ............... 536/22.1; 536/23.1; 536/24.5; 536/26.1; 536/27.1; 514/42; 514/43; 514/44 A

(58) Field of Classification Search .................. None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |

(Continued)

FOREIGN PATENT DOCUMENTS

| | | |
|---|---|---|
| WO | WO 94/02499 | 2/1994 |
| WO | WO 94/17093 | 8/1994 |
| WO | WO 02/36743 | 5/2002 |
| WO | WO 2005121372 | 11/2005 |
| WO | WO 2005121371 | 12/2005 |

OTHER PUBLICATIONS

Kumar et al., Journal of Organic Chemistry, vol. 71(11), 2006, pp. 4188-4201.*

Barany et al., "A New Amino Protecting Group Removable by Reduction. Chemistry of Dithiasuccinoyl (Dts) Function" J. Am. Chem. Soc. (1977) 99:7363-7365.

Barany et al., "Kinetics and Mechanism of the Thiolytic Removal of Dithiasuccinoyl (Dts) Amino Protecting Group" J. Am. Chem. Soc. (1980) 102(9):3084-3095.

(Continued)

*Primary Examiner* — Traviss C McIntosh, III
(74) *Attorney, Agent, or Firm* — Isis Pharmaceuticals, Inc. Patent Dept

(57) ABSTRACT

Provided herein are bicyeMc nucleosides comprising a substituted amino group in the bridge, oligomeric compounds having at least one of these bicyclic nucleosides and methods of using the oligomeric compounds. The bicyclic nucleosides comprising a substituted amino group in the bridge are useful for enhancing properties of oligomeric compounds including nuclease resistance, in certain embodiments, the oligomeric compounds hybridize to a portion of a target RNA resulting in loss of normal function of the target RNA.

30 Claims, No Drawings

U.S. PATENT DOCUMENTS

| | | | |
|---|---|---|---|
| 5,403,711 A | 4/1995 | Walder et al. | |
| 5,405,938 A | 4/1995 | Summerton et al. | |
| 5,405,939 A | 4/1995 | Suhadolnik et al. | |
| 5,432,272 A | 7/1995 | Benner | |
| 5,434,257 A | 7/1995 | Matteucci et al. | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,508,270 A | 4/1996 | Baxter et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,525,711 A | 6/1996 | Hawkins et al. | |
| 5,527,899 A | 6/1996 | Froehler | |
| 5,536,821 A | 7/1996 | Agrawal et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,350 A | 10/1996 | Kmiec | |
| 5,565,555 A | 10/1996 | Froehler et al. | |
| 5,567,811 A | 10/1996 | Misiura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,086 A | 1/1997 | Matteucci et al. | |
| 5,596,091 A | 1/1997 | Switzer | |
| 5,597,909 A | 1/1997 | Urdea et al. | |
| 5,600,032 A | 2/1997 | Sato et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci et al. | |
| 5,652,355 A | 7/1997 | Metelev et al. | |
| 5,652,356 A | 7/1997 | Agrawal | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,700,922 A | 12/1997 | Cook | |
| 5,721,218 A | 2/1998 | Froehler | |
| 5,763,588 A | 6/1998 | Matteucci et al. | |
| 5,792,608 A | 8/1998 | Swaminathan et al. | |
| 5,792,747 A | 8/1998 | Schally et al. | |
| 5,830,653 A | 11/1998 | Froehler et al. | |
| 6,005,096 A | 12/1999 | Matteucci et al. | |
| 6,268,490 B1 | 7/2001 | Imanishi et al. | |
| 6,426,220 B1 | 7/2002 | Bennett et al. | |
| 6,770,748 B2 | 8/2004 | Imanishi et al. | |
| 6,794,499 B2 | 9/2004 | Wengel et al. | |
| 7,053,207 B2 | 5/2006 | Wengel | |
| 8,124,745 B2 * | 2/2012 | Allerson et al. | 536/22.1 |
| 2003/0082807 A1 | 5/2003 | Wengel | |
| 2003/0207841 A1 | 11/2003 | Kaneko et al. | |
| 2003/0224377 A1 | 12/2003 | Wengel et al. | |
| 2004/0014959 A1 | 1/2004 | Sorensen et al. | |
| 2004/0143114 A1 | 7/2004 | Imanishi et al. | |
| 2004/0192918 A1 | 9/2004 | Imanishi et al. | |
| 2004/0219565 A1 | 11/2004 | Kauppinen et al. | |

OTHER PUBLICATIONS

Bass et al., "Double-Stranded RNA as a Template for Gene Silencing" Cell (2000) 101:235-238.

Beaucage et al., "The Functionalization of Oligonucleotides Via Phosphoroamidite Derivatives" Tetrahedron (1993) 49(10):1925-1963.

Beaucage et al., "The Synthesis of Specific Ribonucleotides and Unrelated Phosphorylated Biomolecules by the Phosphoramidite Method" Tetrahedron (1993) 49(46):10441-10488.

Beaucage et al., "Advances in the Synthesis of Oligonucleotides by the Phosphoramidite Approach" Tetrahedron (1992) 48(12):2223-2311.

Brazma, "Gene expression data analysis" FEBS Lett. (2000) 480:17-24.

Carulli et al., "High Throughput Analysis of Differential Gene Expression" J. Cell. Biochem. Suppl. (1998) 31:286-296.

Celis et al., "Gene expression profiling: monitoring transcription and translation products using DNA microarrays and proteomics" FEBS Lett. (2000) 480:2-16.

Chiang et al., "Antisense Oligonucleotides Inhibit Intercellular Adhesion Molecule I Expression by Two Distinct Mechanisms" J. Biol. Chem. (1991) 266(27):18162-18171.

Eckstein (ed.), "Oligonucleotides attached to intercalators, photoreactive and cleavage agents" Oligonucleotides and Analogues, a Practical Approach, Oxford University Press, New York (1991).

Elbashir et al., "Duplexes of 21-nucleotide RNAs mediate RNA interference in cultured mammalian cells" Nature (2001) 411:494-498.

Elbashir et al., "RNA interference is mediated by 21-and 22-nucleotide RNAs" Genes Dev. (2001) 15:188-200.

Englisch et al., "Chemically Modified Oligonucleotides as Probes and Inhibitors" Angewandte Chemie, International Edition (1991) 30:613.

Fire et al., "Potent and specific genetic interference by double-stranded RNA in Caenorhabditis elegans" Nature (1998) 391:806-811.

Fuchs et al., "Identification of Differentially Expressed Genes by Mutually Subtracted RNA Fingerprinting" Anal. Biochem. (2000) 286:91-98.

Gait et al., "Applications of Chemically Synthesized RNA" in RNA: Protein Interactions, Ed. Smith (1998) 1-36.

Gallo et al., "2'-C-Methyluridine phosphoramidite: a new building block for the preparation of RNA analogues carrying the 2'-hydroxyl group" Tetrahedron (2001) 57:5707-5713.

Going et al., "Molecular Pathology and Future Developments" Eur. J. Cancer (1999) 35(14):1895-1904.

Jungblut et al., "Proteomics in human disease: Cancer, heart and infectious diseases" Electrophoresis (1999) 20:2100-2110.

Jurecic et al., "Long-distance DD-PCR and cDNA microarrays" Curr. Opin. Microbiol. (2000) 3:316-321.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kroschwitz, The Concise Encyclopedia of Polymer Science and Engineering, John Wiley & Sons, 1990, pp. 858-859.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotechnol. (2000) 80:143-157.

Madden et al., "Serial analysis of gene expression: from gene discovery to target identification" Drug Discov. Today (2000) 5:415-425.

Miura et al., "Fluorometric determination of total mRNA with olig(dT) immobilized on microtiter plates" Clin. Chem. (1996) 42(11):1758-1764.

Montgomery et al., "RNA as a target of double-stranded RNA-mediated genetic interference in Caenorhabditis elegans" PNAS (1998) 95:15502-15507.

Nishikura et al., "A Short Primer on RNAi: RNA-Directed RNA Polymerase Acts as a Key Catalyst" Cell (2001) 107:415-416.

Prashar et al., "READS: A Method for Display of 3'-End Fragments of Restriction Enzyme-Digested cDNAs for Analysis of Differential Gene Expression" Methods Enzymol. (1999) 303:258-272.

Sanghvi etal., Antisense Research and Applications, Crooke & Lebleu ed., CRC Press, 1993, Chapter 15.

Scaringe, "RNA Oligonucleotide Synthesis via 5'-Silyl-2'-Orthoester Chemistry" Methods (2001) 23:206-217.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63(26):10035-10039.

Sutcliffe et al., "TOGA: An automated parsing technology for analyzing expression of nearly all genes" PNAS (2000) 97(5):1976-1981.

Swayze et al., "Antisense oligonucleotides containing locked nucleic acid improve potency but cause significant hepatotoxicity in animals" Nucl. Acids Res. (2007) 35(2):687-700.

Tabara et al., "RNAi in *C. elegans*: Soaking in the Genome Sequence" Science (1998) 282:430-431.

Tijsterman et al., "RNA Helicase MUT-14-Dependent Gene Silencing Triggered in *C. elegans* by Short Antisense RNAs" Science (2002) 295:694-697.

Timmons et al., "Specific interference by ingested dsRNA" Nature (1998) 395:854.

Timmons et al., "Ingestion of bacterially expressed dsRNAs can produce specific and potent genetic interference in Caenorhabditis elegans" Gene (2001) 263:103-112.

To, "Identification of Differential Gene Expression by High Throughput Analysis" Comb. Chem. High Throughput Screen (2000) 3:235-241.

Tuschl et al., "Targeted mRNA degradation by double-stranded RNA in vitro" Genes Dev. (1999) 13:3191-3197.

Wahlestedt et al., "Potent and nontoxic antisense oligonucleotides containing locked nucleic acids" PNAS (2000) 97(10):5633-5638.

* cited by examiner

SEQUENCE LISTING

```
<160> NUMBER OF SEQ ID NOS: 9

<210> SEQ ID NO 1
<211> LENGTH: 3160
<212> TYPE: DNA
<213> ORGANISM: H. sapiens

<400> SEQUENCE: 1 cctccctcg  cccggcgcgg  tcccgtccgc  ctctcgctcg  cctcccgcct  ccccctcggtc   60 ttccgaggcg  cccgggctcc  cggcgcggcg  gcggaggggg  cgggcaggcc  ggcgggcggt  120
gatgtggcag  gactctttat  gcgctgcggc  aggatacgcg  ctcggcgctg  ggacgcgact  180
gcgctcagtt  ctctcctctc  ggaagctgca  gccatgatgg  aagtttgaga  gttgagccgc  240
tgtgaggcga  ggccgggctc  aggcgaggga  gatgagagac  ggcggcggcc  gcggcccgga  300
gcccctctca  gcgcctgtga  gcagccgcgg  gggcagcgcc  ctcggggagc  cggccggcct  360 gcggcggcg  cagcggcggc  gtttctcgcc  tcctcttcgt  cttttctaac  cgtgcagcct  420
cttcctcggc  ttctcctgaa  agggaaggtg  gaagccgtgg  gctcgggcgg  gagccggctg  480
aggcgcggcg  gcggcggcgg  cggcacctcc  cgctcctgga  gcgggggga  gaagcggcgg  540 cggcggcggc  cgcggcggct  gcagctccag  ggaggggtc  tgagtcgcct  gtcaccattt  600
ccagggctgg  gaacgccgga  gagttggtct  ctcccttct  actgcctcca  acacggcggc  660
ggcggcggcg  gcacatccag  ggacccgggc  cggttttaaa  cctcccgtcc  gccgccgccg  720 cacccccgt  ggcccgggct  ccggaggccg  ccggcggagg  cagccgttcg  gaggattatt  780
cgtcttctcc  ccattccgct  gccgccgctg  ccaggcctct  ggctgctgag  gagaagcagg  840
cccagtcgct  gcaaccatcc  agcagccgcc  gcagcagcca  ttaccggct  gcggtccaga  900 gccaagcggc  ggcagagcga  ggggcatcag  ctaccgccaa  gtccagagcc  atttccatcc  960
tgcagaagaa  gccccgccac  cagcagcttc  tgccatctct  ctcctccttt  tcttcagcc  1020 acaggctccc  agacatgaca  gccatcatca  aagagatcgt  tagcagaaac  aaaaggagat  1080
atcaagagga  tggattcgac  ttagacttga  cctatattta  tccaaacatt  attgctatgg  1140
```

```
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa cccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaaccttt gatgaagatc    2220 agcatacaca aattacaaaa gtctgaattt tttttatca agagggataa acaccatga    2280 aaataaactt gaataaactg aaaatggacc ttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatatacctt tttgtgtcaa aaggacattt aaaattcaat taggattaat aaagatggca    2520 cttttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc taccccttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt tttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga acacagcaa caatgactta    3060 accatataaa tgtggaggct atcaacaaag aatgggcttg aaacattata aaaattgaca    3120
atgatttatt aaatatgttt tctcaattgt aaaaaaaaaa                         3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                          26
```

```
<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                             25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                        30

<210> SEQ ID NO 5
<211> LENGTH: 14
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: 2, 14
<223> OTHER INFORMATION: Bases at these position are RNA

<400> SEQUENCE: 5
cutagcactg gccu                                                         14

<210> SEQ ID NO 6
<211> LENGTH: 14
<212> TYPE: DNA
<213> ORGANISM: Artificial Sequence
<220> FEATURE:
<223> OTHER INFORMATION: Oligomeric compound

<400> SEQUENCE: 6
tcatggctgc agct                                                         14

<210> SEQ ID NO 7
<211> LENGTH: 14
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: 1, 14
<223> OTHER INFORMATION: Bases at these positions are RNA

<400> SEQUENCE: 7
ucatggctgc agcu                                                         14

<210> SEQ ID NO 8
<211> LENGTH: 12
<212> TYPE: DNA
<213> ORGANISM: Artificial Sequence
<220> FEATURE:
<223> OTHER INFORMATION: Oligomeric compound

<400> SEQUENCE: 8
tttttttttt tt                                                           12
```

```
<210> SEQ ID NO 9
<211> LENGTH: 12
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: 11, 12
<223> OTHER INFORMATION: Bases at these positions are RNA

<400> SEQUENCE: 9
tttttttttt uu                                                        12
```

N-SUBSTITUTED-AMINOMETHYLENE BRIDGED BICYCLIC NUCLEIC ACID ANALOGS

CROSS-REFERENCE TO RELATED APPLICATIONS

This application claims priority benefit to U.S. Provisional Application No. 60/940,835, filed May 30, 2007 and entitled, "N-Alkoxyamino Bicyclic Nucleic Acid Analogs" the entirety of which disclosure is incorporated herein by reference.

SEQUENCE LISTING

This application is the national phase entry pursuant to 35 U.S.C. §371 of International Application No. PCT/US2008/064591, filed May 22, 2008, which claims the benefit of U.S. Provisional Application No. 60/940,835, filed May 30, 2007, all of which are incorporated herein in their entireties by reference.

FIELD OF THE INVENTION

Provided herein are bicyclic nucleosides comprising a substituted amino group in the bridge, oligomeric compounds having at least one of these bicyclic nucleosides and methods of using the oligomeric compounds. In certain embodiments, the oligomeric compounds hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely incorporated into antisense oligomeric compounds to enhance one or more properties such as nuclease resistance or binding affinity. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

One recent publication discloses significant hepatotoxicity in animals treated with antisense oligonucleotides containing locked nucleic acids (see, e.g., Swayze et al., Nucl. Acids Res., 2007, 35(2), 687-700).

Consequently, there remains a long-felt need for agents that specifically regulate gene expression via antisense mechanisms. Disclosed herein are N-substituted aminomethylene bridged bicyclic nucleic acid analogs and antisense oligomeric compounds prepared therefrom useful for modulating gene expression pathways, including those relying on mechanisms of action such as RNaseH, RNAi and dsRNA enzymes, as well as other antisense mechanisms based on target degradation or target occupancy. One having skill in the art, once armed with the present disclosure will be able, without undue experimentation, to identify, prepare and exploit antisense compounds for these uses.

BRIEF SUMMARY OF THE INVENTION

In certain embodiments, bicyclic nucleosides are provided having Formula I:

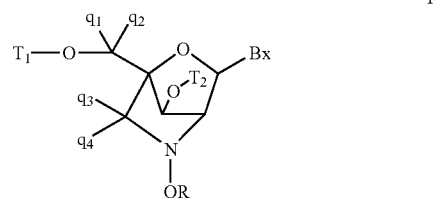

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

R is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_1$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_1$-$C_6$ alkyl, $C_2$-$C_6$ alkenyl, $C_1$-$C_6$ alkynyl, $C_1$-$C_6$ aminoalkyl or a protecting group.

In certain embodiments, R is $C_1$-$C_6$ alkyl or substituted $C_1$-$C_6$ alkyl. In certain embodiments, R is $C_1$-$C_3$ alkyl. In certain embodiments, R is methyl. In certain embodiments, R is substituted $C_1$-$C_3$ alkyl. In certain embodiments, R is —(CH$_2$)$_n$O(CH$_2$)$_m$CH$_3$, wherein n is from 1 to 3 and m is 0 or from 1 to 3. In certain embodiments, R is —(CH$_2$)$_2$OCH$_3$.

In certain embodiments, bicyclic nucleosides having formula I are provided having a the configuration shown in Formula Ia:

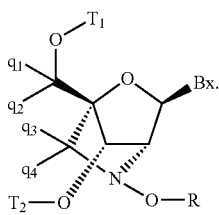

Ia

In certain embodiments, bicyclic nucleosides having formula I are provided having a the configuration shown in Formula Ib:

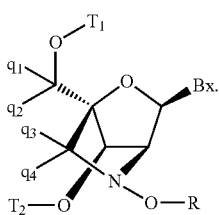

Ib

In certain embodiments, $q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl. In certain embodiments, one of $q_1$ and $q_2$ is H. In certain embodiments, $q_1$ and $q_2$ are each H.

In certain embodiments, $q_3$ and $q_4$ are each, independently, H, $C_1$-$C_6$ alkyl, substituted $C_1$-$C_6$ alkyl, $C_2$-$C_6$ alkenyl substituted $C_2$-$C_6$ alkenyl, $C_1$-$C_6$ alkynyl or substituted $C_2$-$C_6$ alkynyl. In certain embodiments, one of $q_3$ and $q_4$ is H. In certain embodiments, $q_3$ and $q_4$ are each H.

In certain embodiments, one of $q_1$, $q_2$, $q_3$ and $q_4$ is $CH_3$ and the other three of $q_1$, $q_2$, $q_3$ and $q_4$ are independently H. In certain embodiments, one of $q_1$ and $q_2$ is $CH_3$ and one of $q_3$ and $q_4$ is $CH_3$ and the other two of $q_1$, $q_2$, $q_3$ and $q_4$ are independently H.

In certain embodiments, $T_1$ and $T_2$ are each, independently, a hydroxyl protecting group. In certain embodiments, each of said hydroxyl protecting groups is, independently, acetyl, t-butyl, t-butoxymethyl, methoxymethyl, tetrahydropyranyl, 1-ethoxyethyl, 1-(2-chloroethoxy)-ethyl, 2-trimethylsilyl-ethyl, p-chlorophenyl, 2,4-dinitrophenyl, benzyl, benzoyl, p-phenyl-benzoyl, 2,6-dichlorobenzyl, diphenylmethyl, p-nitrobenzyl, triphenylmethyl(trityl), 4-methoxy-trityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl or substituted pixyl. In certain embodiments, $T_1$ is acetyl, benzyl, t-butyldimethylsilyl, t-butyldiphenylsilyl or dimethoxytrityl. In certain embodiments, $T_1$ is 4,4'-dimethoxytrityl. In certain embodiments, $T_2$ is a reactive phosphorus group. In certain embodiments, $T_2$ is diisopropylcyanoethoxy phosphoramidite or H-phosphonate. In certain embodiments, $T_1$ is 4,4'-dimethoxytrityl and $T_2$ is diisopropylcyanoethoxy phosphoramidite.

In certain embodiments, Bx is uracil, thymine, cytosine, adenine or guanine. In certain embodiments, Bx is a pyrimidine, substituted pyrimidine, purine or substituted purine. In certain embodiments, Bx is uracil, 5-methyluracil, 5-methylcytosine, 5-thiazolo-uracil, 5-thiazolo-cytosine or 2,6-diaminopurine. In certain embodiments, Bx is uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one.

In certain embodiments, each $J_1$ and $J_2$ is, independently, H or $C_1$-$C_3$ alkyl.

In certain embodiments, oligomeric compounds are provided comprising at least one bicyclic nucleoside having Formula II:

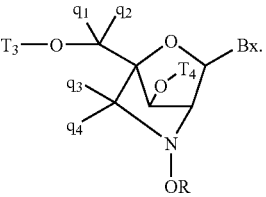

II wherein for each of said at least one bicyclic nucleoside having Formula II:

Bx is a heterocyclic base moiety;

$T_3$ and $T_4$ are each, independently, an internucleoside linking group linking the bicyclic nucleoside to the oligomeric compound or one of $T_3$ and $T_4$ is an internucleoside linking group linking the bicyclic nucleoside to the oligomeric compound and the other of $T_3$ and $T_4$ is H, a hydroxyl protecting group, a linked conjugate group or a 5' or 3'-terminal group;

R is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_1$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_1$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_1$-$C_6$ alkyl, $C_2$-$C_6$ alkenyl, $C_1$-$C_6$ alkynyl, $C_1$-$C_6$ aminoalkyl or a protecting group.

In certain embodiments, R is $C_1$-$C_6$ alkyl or substituted $C_1$-$C_6$ alkyl. In certain embodiments, R is $C_1$-$C_3$ alkyl. In certain embodiments, R is methyl. In certain embodiments, R is substituted $C_1$-$C_3$ alkyl. In certain embodiments, R is —$(CH_2)_n$O$(CH_2)_m$$CH_3$, wherein n is from 1 to 3 and m is 0 or from 1 to 3. In certain embodiments, R is —$(CH_2)_2$O$CH_3$.

In certain embodiments, oligomeric compounds are provided having at least one bicyclic nucleoside of Formula II wherein each nucleoside of Formula II further has the configuration shown in Formula IIa:

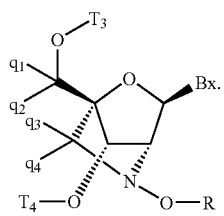

IIa

In certain embodiments, oligomeric compounds are provided having at least one bicyclic nucleoside of Formula II wherein each nucleoside of Formula II further has the configuration shown in Formula IIb:

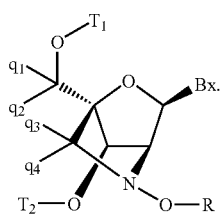

IIb

In certain embodiments, each $q_1$ and $q_2$ is, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl. In certain embodiments, $q_3$ or each $q_2$ is H. In certain embodiments, each $q_3$ and each $q_2$ is H.

In certain embodiments, each $q_3$ and $q_4$ is, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl. In certain embodiments, each $q_3$ or each $q_4$ is H. In certain embodiments, each $q_3$ and each $q_4$ is H.

In certain embodiments, one of each $q_1$, $q_2$, $q_3$ or $q_4$ is $CH_3$ and the other three of each $q_1$, $q_2$, $q_3$ or $q_4$ are each H. In certain embodiments, one of each $q_1$ or $q_2$ is $CH_3$ and one of each $q_3$ of $q_4$ is $CH_3$ and the other two of each $q_1$, $q_2$, $q_3$ or $q_4$ are each H.

In certain embodiments, at least one of $T_3$ and $T_4$ is a 5' or 3' terminal group. In certain embodiments, at least one of $T_3$ and $T_4$ is a conjugate group.

In certain embodiments, each internucleoside linking group is, independently, a phosphodiester or a phosphorothioate. In certain embodiments, each internucleoside linking group is a phosphodiester. In certain embodiments, each internucleoside linking group is a phosphorothioate.

In certain embodiments, oligomeric compounds are provided comprising at least one region of at least two contiguous bicyclic nucleosides having formula II. In certain embodiments, oligomeric compounds are provided comprising at least one region of at least two contiguous bicyclic nucleosides having formula II wherein the at least one region is located at either the 3' or the 5'-end of the oligomeric compound. In certain embodiments, oligomeric compounds are provided comprising at least one region of at least two contiguous bicyclic nucleosides having formula II wherein the at least one region is located at either the 3' or the 5'-end of the oligomeric compound and at least one bicyclic nucleoside having Formula II located at the other of the 3' or the 5'-end of the oligomeric compound. In certain embodiments, oligomeric compounds are provided comprising at least one region of at least two contiguous bicyclic nucleosides having formula II wherein the at least one region is located internally in said oligomeric compound.

In certain embodiments, oligomeric compounds are provided each comprising at least two regions of from 1 to about 5 contiguous bicyclic nucleosides having Formula II wherein the two regions are separated by at least one nucleoside or modified nucleoside. In certain embodiments, gapped oligomeric compounds are provided, each of which comprise at least two external regions of from 1 to about 5 contiguous bicyclic nucleosides having Formula II, wherein one of the external regions is located at the 5'-end, the other of the external regions is located at the 3'-end with an internal region separating the two external regions, the internal region comprising from about 6 to about 14 monomeric subunits. In certain embodiments the internal region comprises from 6 to about 14 monomeric subunits independently selected from nucleo-sides and modified nucleosides.

In certain embodiments, oligomeric compounds are provided each comprising at least two regions of from 1 to about 5 contiguous bicyclic nucleosides having Formula II wherein the two regions are separated by an internal region wherein essentially each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, the internal region comprises from about 10 to about 14 β-D-2'-deoxyribonucleosides.

In certain embodiments, gapped oligomeric compounds are provided wherein the external regions independently comprises from 2 to about 3 bicyclic nucleosides having Formula II and the internal region comprises from about 6 to about 14 monomeric subunits wherein essentially each monomeric subunit in the internal region is a β-D-2'-deoxyribonucleoside. In certain embodiments, gapped oligomeric compounds are provided wherein the external regions independently comprises 2 bicyclic nucleosides having Formula II and the internal region comprises from about 6 to about 14 monomeric subunits wherein essentially each monomeric subunit in the internal region is a β-D-2'-deoxyribonucleoside. In certain embodiments, gapped oligomeric compounds are provided wherein the external regions independently comprises 2 bicyclic nucleosides having Formula II and the internal region comprises 10 β-D-2'-deoxyribonucleosides.

In certain embodiments, oligomeric compounds are provided comprising at least two regions of from 1 to about 5 contiguous bicyclic nucleosides having Formula IIa comprising a gapped oligomeric compound wherein one of said regions of bicyclic nucleosides having Formula II is located at the 5'-end and the other of said regions is located externally at the 3'-end and wherein the two external regions are separated by an internal region comprising from about 6 to about 14 monomeric subunits wherein essentially each monomeric subunit in the internal region is a β-D-2'-deoxyribonucleoside.

In certain embodiments, oligomeric compounds are provided comprising at least two regions of from 1 to about 5 contiguous bicyclic nucleosides having Formula IIb comprising a gapped oligomeric compound wherein one of said regions of bicyclic nucleosides having Formula II is located at the 5'-end and the other of said regions is located externally at the 3'-end and wherein the two external regions are separated by an internal region comprising from about 6 to about 14 monomeric subunits wherein essentially each monomeric subunit in the internal region is a β-D-2'-deoxyribonucleoside.

In certain embodiments, oligomeric compounds are provided comprising from about 8 to about 40 monomers in length. In certain embodiments, oligomeric compounds are provided comprising from about 8 to about 20 monomers in length. In certain embodiments, oligomeric compounds are provided comprising from about 10 to about 16 monomers in length. In certain embodiments, oligomeric compounds are provided comprising from about 12 to about 16 monomers in length. In certain embodiments, oligomeric compounds are provided comprising from about 10 to about 14 monomers in length.

In certain embodiments, oligomeric compounds are provided comprising from about 8 to about 40 nucleosides and/or modified nucleosides or mimetics in length. In certain embodiments, oligomeric compounds are provided comprising from about 8 to about 20 nucleosides and/or modified nucleosides or mimetics in length. In certain embodiments, oligomeric compounds are provided comprising from about 10 to about 16 nucleosides and/or modified nucleosides or mimetics in length. In certain embodiments, oligomeric compounds are provided comprising from about 10 to about 14 nucleosides and/or modified nucleosides or mimetics in length.

In certain embodiments, methods are provided comprising contacting a cell with an oligomeric compound having at least one bicyclic nucleoside of Formula II:

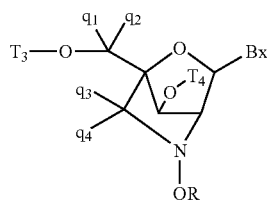

wherein for each of said at least one bicyclic nucleoside having Formula II:

Bx is a heterocyclic base moiety;

$T_3$ and T are each, independently, an internucleoside linking group linking the bicyclic nucleoside to the oligomeric compound or one of $T_3$ and $T_4$ is an internucleoside linking group linking the bicyclic nucleoside to the oligomeric compound and the other of $T_3$ and $T_4$ is H, a hydroxyl protecting group, a linked conjugate group or a 5' or 3'-terminal group;

R is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$; alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein said oligomeric compound comprises from about 8 to about 40 monomeric subunits and is complementary to a target RNA.

In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA.

In certain embodiments, the target RNA is cleaved thereby inhibiting its function. In certain embodiments, the methods comprise evaluating the antisense activity of said oligomeric compound on said cell. In certain embodiments, the evaluating step comprises detecting the levels of target RNA. In certain embodiments, the evaluating step comprises detecting the levels of a protein. In certain embodiments, the evaluating step comprises detection of one or more phenotypic effects.

In certain embodiments, methods of inhibiting gene expression comprising contacting one or more cells, a tissue or an animal with an oligomeric compound of the invention.

The oligomeric compounds comprising at least one bicyclic nucleoside having formula II show good activity both in vitro and in vivo without exhibiting significant hepatotoxicity. The activity of oligomeric compounds having nucleosides with Formula II was about 80% relative to the similar oligomeric compound having 4'-$CH_2$—O-2' BNAs. The oligomeric compounds having nucleosides with Formula II did not exhibit significant hepatotoxicity whereas the oligomeric compound having 4'-$CH_2$—O-2' BNAs did exhibit significant hepatotoxicity at the higher doses. The oligomeric compounds having nucleosides with Formula II also showed about a 37 and 55 fold increase in nuclease resistance relative to oligomeric compounds having 4'-$CH_2$—O-2' BNAs or 2'-MOE modified nucleosides respectively.

DETAILED DESCRIPTION OF THE INVENTION

In certain embodiments, provided herein are bicyclic nucleosides comprising substituted amino groups in the bridge, oligomeric compounds having at least one of these bicyclic nucleosides and methods of using the oligomeric compounds. Methods of preparing the bicyclic nucleosides of the invention are also provided. In certain embodiments, the oligomeric compounds are designed to hybridize to a portion of a target RNA. In certain embodiments, the oligomeric compounds can be used in the design of aptamers which are oligomeric compounds capable of binding to aberrant proteins in an in vivo setting.

In certain embodiments, each of the bicyclic nucleosides have Formula I:

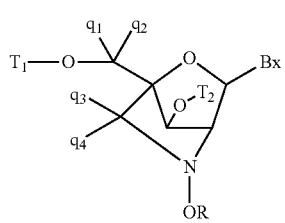

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

R is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, $CN$, $O-C(=O)NJ_1J_2$, $N(H)C(=NH)NJ_1J_2$ or $N(H)C(=X)N(H)J_2$ wherein X is O or S; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, the bicyclic nucleosides are prepared as protected bicyclic nucleoside phosphoramidites for incorporation into oligomeric compounds wherein $T_1$ is a hydroxyl protecting group such as a 4,4'-dimethoxytrityl group and $T_2$ is phosphoramidite such as $-P(O-(CH_2)_2CN)[N(CH(CH_3)_2)_2]$. In certain embodiments, each q is H and R is $C_1$-$C_3$ alkyl preferably methyl or substituted $C_1$-$C_3$ alkyl preferably $-(CH_2)_2OCH_3$.

In certain embodiments, each of the bicyclic nucleosides have the configuration shown in Formula Ia:

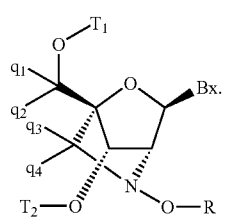

Ia

In certain embodiments, each of the bicyclic nucleosides have the configuration shown in Formula Ib:

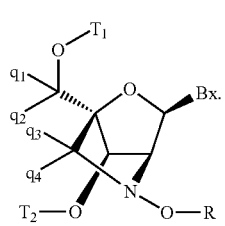

Ib

The bicyclic nucleoside monomers are especially useful for incorporation into oligomeric compounds. Such incorporation has been shown to enhance desired properties of the resulting oligomeric compounds. As shown in some of the examples included herein some of the properties that have been enhanced include nuclease resistance, toxicity profile and therapeutic window. Such oligomeric compounds each comprise at least one bicyclic nucleoside having Formula II:

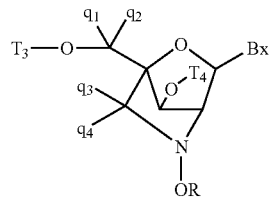

II wherein for each of said at least one bicyclic nucleoside having Formula II:

Bx is a heterocyclic base moiety;

$T_3$ and $T_4$ are each, independently, an internucleoside linking group linking the bicyclic nucleoside to the oligomeric compound or one of $T_3$ and $T_4$ is an internucleoside linking group linking the bicyclic nucleoside to the oligomeric compound and the other of $T_3$ and $T_4$ is H, a hydroxyl protecting group, a linked conjugate group or a 5' or 3'-terminal group;

R is $C_1$-$C_6$ alkyl, substituted $C_1$-$C_6$ alkyl, $C_2$-$C_6$ alkenyl, substituted $C_2$-$C_6$ alkenyl, $C_1$-$C_6$ alkynyl or substituted $C_1$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, $CN$, $O-C(=O)NJ_1J_2$, $N(H)C(=NH)NJ_1J_2$ or $N(H)C(=X)N(H)J_2$ wherein X is O or S; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are prepared wherein each of the bicyclic nucleosides have Formula IIa:

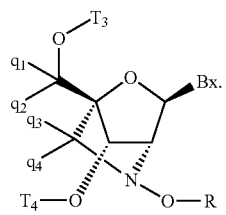

IIa

In certain embodiments, oligomeric compounds are prepared wherein each of the bicyclic nucleosides have Formula IIb:

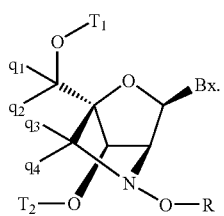

IIb

Methods of using the oligomeric compounds of the invention are also provided. In certain embodiments, methods are provided wherein a cell is contacted with an oligomeric compound of the invention that is complementary to a target RNA. The cell can be in an animal preferably a human. The target RNA is selected from any RNA nucleic acid that would result in some benefit but preferably mRNA, pre-mRNA and micro RNA. In certain embodiments, the target RNA is cleaved, as a result of interaction with an oligomeric compound thereby inhibiting its function. The efficiency of the methods can be evaluated by looking at a variety of criteria or end points such as evaluating the antisense activity by detecting the levels of a target RNA, detecting the level of a protein or by detecting one or more phenotypic effects.

Oligomeric compounds comprising bicyclic nucleosides of formula II were tested for nuclease stability (Example 35), in vitro activity (example 32) and for in vivo activity (Examples 33 and 34). The oligomeric compounds comprising at least one bicyclic nucleoside having formula IIa exhibited good activity both in vitro and in vivo. The observed activity was about 80% relative to a similar oligomeric compounds having 4'-CH$_2$—O-2' bridged BNAs. The oligomeric compounds having nucleosides with Formula II did not exhibit significant hepatotoxicity whereas the oligomeric compounds having 4'-CH$_2$—O-2' bridged BNAs did exhibit significant hepatotoxicity at the higher doses. The oligomeric compounds having nucleosides with Formula II also showed about a 37 and 55 fold increase in nuclease resistance relative to oligomeric compounds having 4'-CH$_2$—O-2' bridged BNAs or 2'-MOE modified nucleosides respectively. Based on the similarities between the oligomeric compounds having either the bicyclic nucleosides of Formula II or the 4'-CH$_2$—O-2' bridged BNAs the increased nuclease resistance and absence of hepatotoxicity is unexpected.

The bicyclic nucleosides having Formula II (N-alkoxyamino, or substituted N-alkoxyamino) bicyclic nucleosides are useful for modifying otherwise unmodified oligomeric compounds at one or more positions. Such modified oligomeric compounds can be described as having a particular motif. Motifs include but are not limited to a gapped motif, a hemimer motif, a blockmer motif, a fully modified motif, a positionally modified motif and an alternating motif. In conjunction with these motifs a wide variety of internucleoside linkages can be used including but not limited to phosphodiester and phosphorothioate internucleoside linkages used uniformly or in combinations. The number and positioning of bicyclic nucleosides having Formula II and the use of various internucleoside linkage strategies can be easily optimized to prepare an oligomeric compound that will provide the best activity for a particular target.

Representative U.S. patents that teach the preparation of representative motifs include, but are not limited to, U.S. Pat. No. 5,013,830; U.S. Pat. No. 5,149,797; U.S. Pat. No. 5,220, 007; U.S. Pat. No. 5,256,775; U.S. Pat. No. 5,366,878; U.S. Pat. No. 5,403,711; U.S. Pat. No. 5,491,133; U.S. Pat. No. 5,565,350; U.S. Pat. No. 5,623,065; U.S. Pat. No. 5,652,355; U.S. Pat. No. 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

In certain embodiments, gapped oligomeric compounds are provided having one or more bicyclic nucleosides of the above formula II at the 3' and 5'-terminal positions flanking an internal region of nucleosides. In certain embodiments, the internal nucleosides are β-D-deoxyribonucleosides. In a further embodiment they are β-D-deoxyribonucleosides in combination with one or more other sugar modified nucleosides.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$) aryl, aralkyl, heterocyclic, heteroaryl, heteroarylalkyl, amino (—NR$_{bb}$R$_{cc}$), imino(=NR$_{bb}$), amido (—C(O)N—R$_{bb}$R$_{cc}$ or —N(R$_{bb}$)C(O)R$_{aa}$), azido (—N$_3$), nitro (—NO$_2$), cyano (—CN), carbamido (—OC(O)NR$_{bb}$R$_{cc}$ or —N(R$_{bb}$)C(O)OR$_{aa}$), ureido (—N(R$_{bb}$)C(O)NR$_{bb}$R$_{cc}$), thioureido (—N(R$_{bb}$)C(S)NR$_{bb}$R$_{cc}$), guanidinyl —N(R$_{bb}$)C(=NR$_{bb}$)NR$_{bb}$R$_{cc}$), amidinyl (—C(=NR$_{bb}$)NR$_{bb}$R$_{cc}$ or —N(R$_{bb}$)C(NR$_{bb}$)R$_{aa}$), thiol (—SR$_{bb}$), sulfinyl (—S(O)R$_{bb}$), sulfonyl (—S(O)$_2$R$_{bb}$), sulfonamidyl (—S(O)$_2$NR$_{bb}$R$_{cc}$ or —N(R$_{bb}$)—S(O)$_2$R$_{bb}$) and conjugate groups. Wherein each R$_{aa}$, R$_{bb}$ and R$_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclc" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups. The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "oxo" refers to the group (=O).

The terms "bicyclic nucleic acid", "BNA", "bicyclic nucleoside" or "bicyclic nucleotide" refer to a nucleoside or nucleotide wherein, the furanose portion of the nucleoside includes a bridge connecting two carbon atoms on the furanose ring, thereby forming a bicyclic ring system.

The term "gapmer" or "gapped oligomeric compound" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments, the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleosides in the gap are unmodified and nucleosides in the wings are modified. In certain embodiments, the modifications are N-alkoxyamino bicyclic nucleosides.

The term "motif" refers to the pattern of unmodified and modified nucleotides in an antisense compound.

The term "chimeric oligomeric compound" or "chimeric oligonucleotide" refers to an oligomeric compound or an oligonucleotide having at least one sugar, nucleobase or internucleoside linkage that is modified relative to naturally occurring linked nucleosides. The remainder of the sugars, nucleobases and internucleoside linkages can be independently modified or unmodified wherein each nucleoside and linkage can be the same or different.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmakokinetics or pharmakodynamic of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In certain embodiments, oligomeric compounds are modified by covalent attachment of one or more conjugate groups. In general, conjugate groups modify one or more properties of the attached oligomeric compound including but not limited to pharmakodynamic, pharmakokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Linking groups and bifunctional linking moieties such as those known in the art are useful herein for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy) ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate chloroacetyl, trichloroacetyl, trifluoroacetyl, pivaloyl, benzoyl, p-phenylbenzoyl, 9-fluorenylmethyl carbonate, mesylate, tosylate, triphenylmethyl(trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyl-diphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)-ethoxycarbonyl (Bpoc), t-butoxycarbonyl (BOC), allyloxycarbonyl (Alloc), 9-fluorenylmethyl-oxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

In certain embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In certain embodiments, oligomeric compounds are provided having reactive phosphorus groups useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^V$ state using known methods to yield, in certain embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-CH$_2$—C(=O)—N(H)-5'), amide-4 (3'-CH—N(H)—C(=O)-5').

Specific examples of oligomeric compounds useful in this invention include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555, 5,527,899; 5,721,218;

5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

As used herein the phrase "neutral internucleoside linkage" is intended to include internucleoside linkages that are non-ionic. Neutral internucleoside linkages include but are not limited to phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and $CH_2$ component parts.

Bicyclic nucleosides having Formula I as described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyena Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry. In 9 Volumes*, Barry M. Trost, Editor-in-Chief, Pergamon Press, New York (1993); *Advanced Organic Chemistry, Part B: Reactions and Synthesis,* 4th Ed.; Carey and Sundberg; Kluwer Academic/Plenum Publishers: New York (2001); *Advanced Organic Chemistry, Reactions, Mechanisms, and Structure* 2nd Edition, March, McGraw Hill (1977); *Protecting Groups in Organic Synthesis,* 2nd Edition, Greene, T. W., and Wutz, P. G. M., John Wiley & Sons, New York (1991); and *Comprehensive Organic Transformations,* 2nd Edition, Larock, R. C., John Wiley & Sons, New York (1999).

The compounds described herein contain at least one asymmetric center and thus give rise to enantiomers, diastereomers, and other stereoisomneric forms that may be defined, in terms of absolute stereochemistry, as (R)- or (S)-, α or β, or as (D)- or (L)- such as for amino acids. It is intended that all such possible isomers, as well as their racemic and optically pure forms be included herein. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In certain embodiments, the term "oligomeric compound" refers to a polymer comprising linked monomeric subunits having at least a region that is capable of hybridizing to a nucleic acid molecule. The term "oligomeric compound" includes polymers comprising linked monomeric subunits wherein the monomeric subunits include nucleosides, modified nucleosides, nucleoside analogs, nucleoside mimetics as well as non-nucleic acid components such as conjugate groups. In certain embodiments, mixtures of monomeric subunits such as but not limited to those listed provide oligomeric compounds having enhanced properties for uses such as therapeutics and diagnostics. Bicyclic nucleosides having formula I would be referred to as a modified nucleoside or bicyclic nucleoside as the furanose ring system and the heterocyclic base remain intact. The monomeric subunits can be linked by naturally occurring phosphodiester internucleoside linkages or alternatively by any of a plurality of internucleoside linkages disclosed herein such as but not limited to phosphorothioate internucleoside linkages or mixtures thereof.

In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moeities can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

Oligomeric compounds are routinely prepared linearly but can be joined or otherwise prepared to be circular and may also include branching. Oligomeric compounds can combined to form double stranded constructs such as for example two strands hybridized to form double stranded compositions. The double stranded compositions can be linked or separate and can include overhangs on the ends.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2',3' or 5' hydroxyl moiety of the sugar, in forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof." In general, a nucleobase is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases also include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Oligomeric compounds may also contain one or more nucleosides having modified sugar moieties. The furanosyl sugar ring can be modified in a number of ways including substitution with a substituent group (2',3',4' or 5'), bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCI/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ (2'-MOE or simply MOE) substituent group; 4'-thio modified sugars and bicyclic modified sugars.

As used herein the term "nucleoside mimetic" or simply "mimetic" is intended to include those structures used to replace the sugar, the sugar and the base or the sugar the base and the internucleoside linkage. A sugar mimetic would include structures such as but not limited to the cyclohexitol ring or morpholino ring replacing the sugar furanose ring but maintaining a heterocyclic base for hybridization and is linked phosphodiester internucleoside linkage. A nucleotide mimetic would include structures such as but not limited to peptide nucleic acids or morpholinos (morpholinos linked by —N(H)—C(=O)—O— or other non-phosphodiester linkage) wherein the sugar and the internucleoside linkage have been replaced. In general a mimetic maintains a heterocyclic base for hybridization to another heterocyclic base but the sugar or the sugar and linkage are replaced with groups that are expected to enhance one or more properties in the resulting oligomeric compound.

In certain embodiments, oligomeric compounds are provided comprising from about 8 to about 80 monomer subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds are provided comprising from 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds are provided comprising from 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds are provided comprising from 10 to 16 monomer subunits in length. One having ordinary skill in the art will appreciate that this embodies oligomeric compounds of 10, 11, 12, 13, 14, 15 or 16 monomer subunits in length, or any range therewithin.

In certain embodiments, oligomeric compounds are provided comprising from 12 to 16 monomer subunits in length. One having ordinary skill in the art will appreciate that this embodies oligomeric compounds of 12, 13, 14, 15 or 16 monomer subunits in length, or any range therewithin.

In certain embodiments, oligomeric compounds are provided comprising from 10 to 14 monomer subunits in length. One having ordinary skill in the art will appreciate that this embodies oligomeric compounds of 10, 11, 12, 13 or 14 monomer submits in length, or any range therewithin.

In certain embodiments, oligomeric compounds are provided comprising any of a variety of ranges of lengths of linked monomer subunits. In certain embodiments, oligomeric compounds provided herein consist of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24.20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, oligomeric compounds are provided comprising from 8-16, 8-40, 10-12, 10-14, 10-16, 10-18, 10-20, 10-21, 12-14, 12-16, 12-18, 12-20 and 12-24 linked monomer subunits.

In certain embodiments, oligomeric compounds are prepared according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Carthers U.S. Pat. Nos. 4,415,732; 4,458, 066; 4,500,707; 4,668,777; 4,973,679; and 5,132,418; and Koster U.S. Pat. No. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2-O-t-butyldimethylsilyl (TBDMS), 5'-O-DMT-2'-O-[1(2-fluorophenyl)-4-methoxypiperidin-4-yl](FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries.

The primary groups being used for commercial RNA synthesis are:

TBDMS=5'O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

In certain embodiments, each of the aforementioned RNA synthesis strategies can be used herein. Strategies that would be a hybrid of the above e.g. using a 5'-protecting group from one strategy with a 2'-O-protecting from another strategy are also amenable herein.

In the context of this invention, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds provided herein can c comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, doable-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded compositions, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent.

The suitable target segments may also be combined with their respective complementary antisense oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, oligomeric compounds and targets identified herein may be used in drug discovery efforts to elucidate relationships that exist between proteins and a disease state, phenotype, or condition. These methods include detecting or modulating a target peptide comprising contacting a sample, tissue, cell, or organism with the oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention have a higher affinity for target RNAs than does non-modified DNA. In certain such embodiments, that higher affinity in turn provides increased potency allowing for the administration of lower doses of such compounds, reduced potential for toxicity and improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. The oligomeric compounds provided herein may be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett, 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteonmics (Celis, et al., FEBS Lett., 2000, 480, 2-16; Jungblut, et al., Electrophoresis, 1999, 20, 2100-10), expressed sequence tag (EST) sequencing (Cells, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry, methods (To, Comb. Chem. High Throughput Screen, 2000, 3, 235-41).

While in certain embodiments, oligomeric compounds provided herein can be utilized as described, the following examples serve only to illustrate and are not intended to be limiting.

EXAMPLES

General

The sequences listed in the examples have been annotated to indicate where there are modified nucleosides or internucleoside linkages. All non-annotated nucleosides are 1-D-ribonucleosides linked by phosphodiester internucleoside linkages. Phosphorothioate internucleoside linkages are indicated by underlining. Modified nucleosides are indicated by a subscripted letter following the capital letter indicating the nucleoside. In particular, subscript "m" indicates 2'-O-methyl; subscript "n" indicates N-methoxy-amino BNA; subscript "l" indicates 4'-CH$_2$—O-2' BNA; and subscript "e" indicates 2'-O-methoxyethyl (MOE). For example U$_n$ is a modified uridine having a N-methoxy amino BNA. $^{Me}$C and $^{Me}$U indicate a 5-methyl cytosine ribonucleoside or a 5-methyl uracil ribonucleoside respectively.

Example 1

Preparation of Compound 18 (Scheme 1)

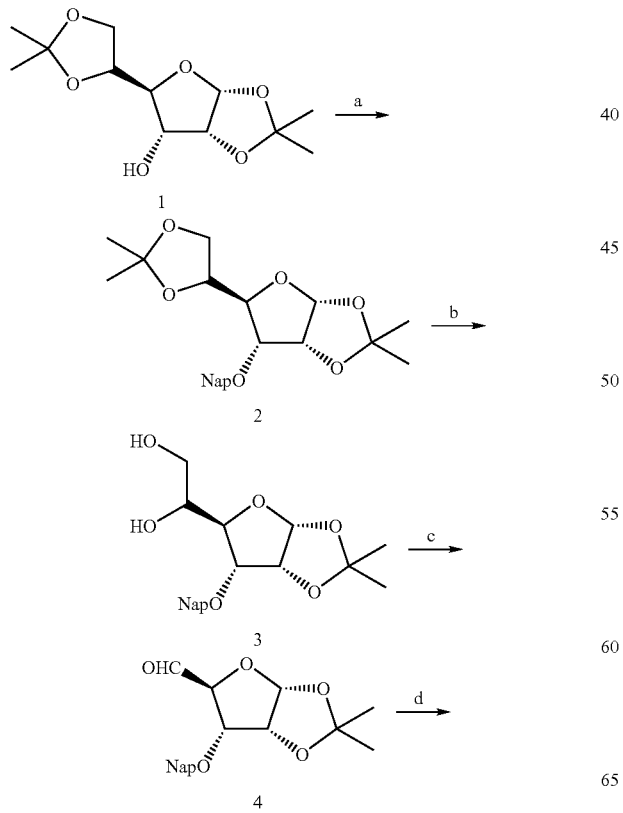

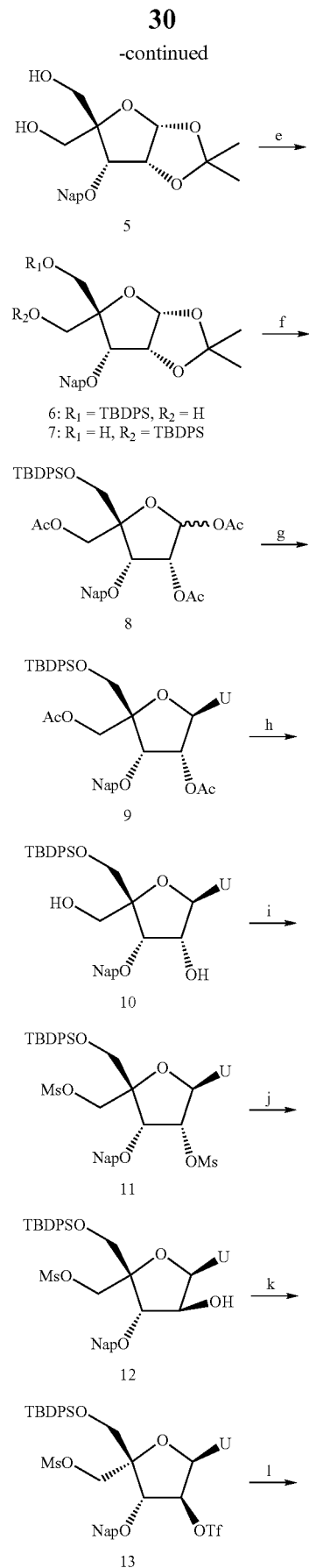

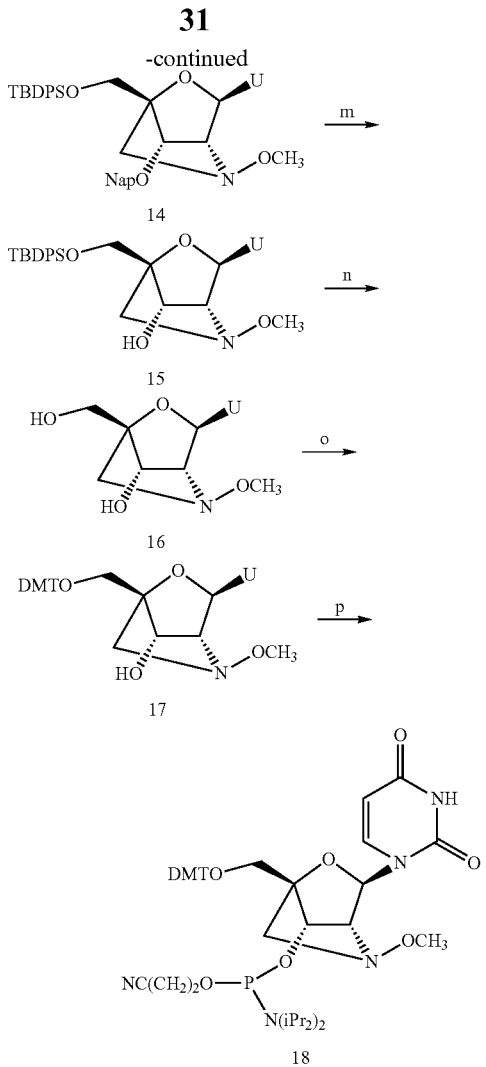

(a) NaH, DMF, 2-(bromomethyl)-naphthalene;
(b) AcOH, H₂O
(c) NaIO₄, CH₂Cl₂;
(d) HCHO, NaOH;
(e) TBDPSCl, Et₃N, DMAP, CH₂Cl₂, rt;
(f) Ac₂O, AcOH, Cat. H₂SO₄;
(g) Uracil, BSA, TMSOTf, CH₃CN, reflux, 2 h;
(h) 7M NH₃ in MeOH, rt;
(j) MsCl, Py, rt, 98%;
(k) i) CH₃CN, DBU, rt, 95%,
  ii) 0.4M aqueous NaOH, dioxane, rt, 85%;
(l) (CF₃SO₂)₂O, DMAP, CH₂Cl₂, -15 to -10° C., 58-64%;
(m) N-methoxyamine, DMF, iPr₂NEt, 60° C., 18 h, 85%;
(n) DDQ, CH₂Cl₂, H₂O, 18 h, rt, 89%
(o) TEA•3HF, TEA, THF, 85%;
(p) DMTCl, Py, rt, 97%;
(q) 2-cyanoethyl-N,N-diisopropylphosphorodiamidite, N-methylimidazole, 1-H-tetrazole, DMF, 94%.

a) Preparation of Compound 2

NaH (60% in mineral oil, 49.2 g, 1.6 equivalents) was added to a 2 L nitrogen flushed round bottom flask and washed with hexanes (2×0.5 L) to remove the mineral oil. After decanting the hexanes, DMF (700 mL) was added and the mixture was cooled in an ice bath. 1,2:5,6-Di-O-isopropylidene-α-D-allofuranose 1 (200 g, 0.77 moles, commercially available from Pfanstiehl Laboratories, Inc.; order #D-126) was added to the reaction and the mixture was stirred for 30 minutes. 2-(Bromomethyl)-naphthalene (187 g, 1.1 equivalent) was slowly added to the reaction mixture over 30 minutes and the stirring was continued at room temperature for another 90 minutes, TLC analysis (30% EtOAc/hexanes, visualized with charring after treatment with anisaldehyde spray reagent) at this time indicated complete consumption of starting material Compound 1. The reaction was poured into cold water (1.5 L), which was in an ice bath. The resulting aqueous mixture was extracted with EtOAc (250 mL×2) and the organic layers were combined, washed with water (1 L), brine (1 L) and concentrated under reduced pressure to a volume of approximately 500 mL. Water was now added to the organic layer and the resulting biphasic mixture was evaporated under reduced pressure (50° C.) until the first signs of precipitate were observed in the aqueous layer. At this time the flask was removed from the rotary evaporator and stirred vigorously using a mechanical stirrer for 1 hour. The light yellow precipitate thus obtained was collected by filtration using a cloth filter. The solid was then suspended in hexanes (1 L), filtered, rinsed with additional hexanes (500 mL) and dried to provide Compound 2 (276 g, 90%) as a white solid. ¹H NMR (300 MHz, CDCl₃) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 3

Compound 2 (115 g, 0.287 moles) was added in small portions to a solution of acetic acid (958 mL) and water (383 mL). The reaction was stirred at room temperature for 16 hours after which, TLC analysis (30% EtOAc/hexanes) indicated complete consumption of Compound 2. The reaction was then concentrated under reduced pressure until most of the acetic acid was removed. The remaining solution was poured, in small portions, into a stirred mixture of EtOAc (1 L) and saturated aqueous NaHCO₃ solution (1 L). Solid sodium bicarbonate was then added to the above mixture until gas evolution ceased. The organic layer was then separated, washed with water (1 L×2), brine (1 L), dried (Na₂SO₄), filtered and concentrated under reduced pressure to provide Compound 3 (102 g) as a yellow foam, which was used without any further purification in the next step.

c) Preparation of Compound 4

Crude Compound 3 (102 g) was dissolved in dioxane (862 mL) and a solution of NaIO₄ (64 g) in water (2.18 L) was added over 40 minutes. After 90 minutes the reaction mixture was poured into EtOAc (1 L) and the organic layer was separated, washed with water (1 L), brine (1 L), dried (Na₂SO₄) and concentrated to provide Compound 4 as a white solid, which was used without further purification in the next step.

d) Preparation of Compound 5

Compound 4 (crude from step C above) was dissolved in a mixture of THF (287 mL) and water (287 mL) and the reaction was cooled in an ice bath. 10 N NaOH (200 mL) and formaldehyde (283 mL of a 37% aqueous solution) were added to the reaction and the stirring was continued at room temperature for approximately 16 hours. The reaction was then poured into EtOAc (500 mL) and washed with water (1 L), brine (1 L) and evaporated under reduced pressure until approximately 100 mL of EtOAc was left (a white precipitate was formed in the process). Et₂O (200 mL) was added to the precipitate and the mixture was stirred for 10 minutes and filtered to provide Compound 5 as a white solid (60 g, 60% from 2). ¹H NMR (300 MHz, CDCl₃) δ 7.85 (m, 4H), 7.48 (m, 3H), 5.75 (d, 1H, J=3.9), 4.96 (d, 1H, J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

e) Preparation of Compounds 6 and 7 tert-Butyldiphenylchlorosilane (45.0 mL, 170 mmol) was added to a cold (0° C.) stirring solution of Compound 5 (50 g, 138 mmol) and triethylamine (27.00 mL, 190 mmol,) in dichloromethane (666 mL). After the addition was complete, the reaction was warmed to room temperature and the stirring was continued for 16 h. MeOH (50 mL) was added (to quench the excess TBDPSCl) to the reaction and the stirring was continued for another 2 h at room temperature. The reaction was then diluted with ethyl acetate (300 mL) and the organic layer was washed with saturated aqueous NaHCO$_3$ (200 mL), brine (200 mL), dried (Na$_2$SO$_4$) and concentrated. The residue obtained was purified by column chromatography (SiO$_2$, 15% to 50% EtOAc in hexanes) to yield compound 6 (45.2 g, 64%, white solid), compound 7 (18.8 g, 26%, viscous oil) and unreacted starting material compound 5 (5.11 g, 10%), Compound 6: $^1$H NMR (300 MHz, CDCl$_3$) δ 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H). Compound 7: $^1$H NMR (300 MHz, CDCl$_3$) δ 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

f) Preparation of Compound 8

Concentrated H$_2$SO$_4$ (2 drops) was added to a solution of Compound 6 (18 g, 30.06 enol) in glacial acetic acid (88 mL) and acetic anhydride (22 mL). After stirring at room temperature for 2 hour, the reaction mixture was poured into ethyl acetate (300 mL) and the organic layer was washed with water (200 ml), saturated NaHCO$_3$ (200 mL), brine (200 mL), dried (Na$_2$SO$_4$) and concentrated under reduced pressure. Purification by column chromatography (SiO$_2$, eluting with 20% to 33% ethyl acetate/exanes) provided Compound 8 (18.53 g, 90%, α/β mixture, 4:1). $^1$H NMR (Major isomer, 300 MHz, CDCl$_3$) 7.85-7.31 (m, 17H), 6.19 (s, 1H), 7.30 (m, 6H), 5.43 (d, J=5.1 Hz, 1H), 4.978-4.68 (m, 2H), 4.56-4.51 (m, 3H), 3.68 (m, 2H), 2.12 (s, 3H), 1.96 (s, 3H), 1.04 (s, overlapping with other isomer, 9H,); MS (ES) m/z 707.1 [M+Na]$^+$.

g) Preparation of Compound 9

Compound 8 (18 g, 26.30 mmol) was mixed with uracil (5.90 g, 52.6 mmol) and dried over P$_2$O$_5$ under reduced pressure over night. The reaction mixture was suspended in anhydrous CH$_3$CN (113 mL) and N,O-Bis(trimethylsilyl)acetamide (38.58 mL, 17.80 mmol) added. After heating at 67° C. for 1.5 h to get a clear solution, the reaction mixture was cooled to 0° C. To this trimethylsilyl triflate (9.52 mL, 52.60 mmol) was added. The reaction mixture was stirred at 0° C. for 15 min then heated at 70° C. for 1.5 h. The reaction mixture was cooled to room temperature and poured into ethyl acetate (200 mL). The organic layer was washed with saturated NaHCO$_3$ (100 mL), brine (100 mL), dried (Na$_2$SO$_4$) and concentrated under reduced pressure. The residue was purified by flash silica gel column chromatography and eluted with 5% methanol in CH$_2$Cl$_2$ to provide Compound 9 (16.85 g, 87%), $^1$H NMR (300 MHz, CDCl$_3$) δ 8.22 (brs, 1H), 7.63-7.08 (m, 18H), 5.98 (d, J=4.9 Hz, 1H), 5.22 (t, J=5.3 Hz, 1H), 5.14 (d, J=7.9 Hz, 1H), 4.54 (d, J=11.5 Hz, 1H), 4.38-4.26 (m, 3H), 3.87 (d, J=12.4 Hz, 1H), 3.70 (d, J=11.3 Hz, 1H), 3.49 (d, J=11.3 Hz, 1H), 1.88 (s, 3H), 1.70 (s, 3H), 0.82 (s, 9H); $^{13}$C NMR (75 MHz, CDCl$_3$) δ 170.6, 170.3, 162.91, 150.2, 140.2, 134.6, 133.4, 132.8, 132.1, 130.5, 130.4, 128.6, 128.2, 128.0, 127.0, 126.6, 126.5, 125.8, 103.1, 87.5, 87.0, 77.4, 77.1, 74.9, 65.0, 63.3, 27.2, 20.9, 19.5; MS (ES) m/z 735.1 [M–H]$^-$.

h) Preparation of Compound 10

Compound 9 (16.7 g, 22.66) was dissolved in methanolic ammonia (7 M, 123 mL). The reaction mixture was stirred at room temperature for 18 h. Solvent was removed under reduced pressure and the residue was purified by column chromatography and eluted with 5% methanol in dichloromethane to yield Compound 10 (14.18 g, 96%). $^1$H NMR (300 MHz, DMSO-d$_6$) δ 11.35 (s, 1H), 7.94-7.89 (m, 4H), 7.59-7.30 (m, 14H), 5.95 (d, J=–5.1 Hz, 1H), 5.74 (d, J=7.4 Hz, 1H), 5.17 (d, J=7.9 Hz, 1H), 5.04 (t, J=5.9 and 5.1 Hz, 1H), 4.97 (d, J=12.0 Hz, 1H), 4.69 (d, J=12.1 Hz, 1H), 4.4-4.38 (m, 1H), 4.26 (d, J=5.9 Hz, 1H), 3.81-3.69 (m, 3H) 3.59-3.53 (m, 1H), 0.93 (s, 9H); $^{13}$C NMR (75 MHz, CDCl$_3$) δ 163.7, 151.2, 140.3, 135.7, 135.5, 134.9, 133.4, 133.3, 132.9, 132.2, 130.3, 130.2, 128.6, 128.2, 128.1, 127.9, 127.2, 126.4, 126.3, 126.1, 102.7, 91.4, 89.2, 76.4, 75.0, 73.5, 65.1, 63.0, 27.1, 19.5; MS (ES) m/z 650.9 [M–H]$^-$.

i) Preparation of Compound 11

The Compound 10 (14 g, 21.46 mmol) was dried over P$_2$O$_5$ under reduced pressure. Methanesulfonyl chloride (7.51 mL, 96.68 mmol) was added to a cold (0° C.) solution of Compound 10 in anhydrous pyridine (118 mL). After stirring at room temperature for 3 h, the reaction mixture was poured into ethyl acetate and the organic layer was sequentially washed with saturated NaHCO$_3$ (400 mL), brine (400 mL), dried (Na$_2$SO$_4$) and concentrated under vacuum. The residue obtained was purified using flash silica gel column chromatography and eluted with 5% MeOH in CH$_2$Cl$_2$ to provide Compound 11 (16.21 g, 93% yield). $^1$H NMR (300 MHz, CDCl$_3$) δ 8.33 (s, 1H), 7.86-7.79 (m, 4H), 7.58-7.28 (m, 14H), 6.13 (d, J=3.6 Hz, 1H), 5.38 (m, 1H), 5.31 (d, J=8.1 Hz, 1H), 4.96 (d, J=11.5 Hz, 1H), 4.65 (d, J=11.3 Hz, 1H), 4.57-4.53 (m, 2H), 4.23 (d, J=11.5 Hz, 1H), 3.98 (d, J=11.3 Hz, 1H) 3.77 (d, J=11.3 Hz, 1H), 3.18 (s, 3H), 2.84 (s, 3H), 1.05 (s, 9H); MS (ES) m z 806.9 [M–H]$^-$.

j) Preparation of Compound 12

To a solution of Compound 11 (16.00 g, 19.74 mmol) in anhydrous CH$_3$CN (135 mL) was added 1,8-diazabicyclo [5.4.0]undec-7-ene (5.46 mL, 39.48 mmol). After stirring at room temperature for 3 h, the mixture was diluted with EtOAc (300 mL), washed with 1% (v/v) aqueous acetic acid (1×400 mL) and brine (2×400 mL), dried over anhydrous Na$_2$SO$_4$, filtered, and evaporated to a foam. The foam was redissolved in 1,4-dioxane (216 mL) and 2 M aqueous NaOH (54 mL) was added. After 45 min, the mixture was neutralized with AcOH, diluted in ethyl acetate (400 mL), washed with saturated aqueous NaHCO$_3$ (1×300 mL) and brine (300 mL), dried over anhydrous Na$_2$SO$_4$, filtered, and evaporated. Purification by silica gel chromatography (5% MeOH in CH$_2$Cl$_2$) yielded Compound 12 (12.25 g, 84.8% yield) as a white foam. $^1$H NMR (300 MHz, DMSO-d$_6$) δ 11.33 (s, 1H), 7.91 (br s, 4H), 7.59-7.34 (m, 14H), 6.22 (d, J=4.9 Hz, 1H), 6.02 (d. J=4.7 Hz, 1H), 5.16 (d, J=8.1 Hz, 1H), 4.97 (d, J=12.2 Hz, 1H), 4.79 (d, J=12.2 Hz, 1H), 4.58-4.50 (m, 2H), 4.40 (d, J=10.4 Hz, 1H), 4.34 (br s, 1H) 3.84 (m, 2H), 3.16 (s, 3H), 0.85 (s, 9H); MS (ES) m/z 731.2 [M+H]$^+$.

k) Preparation of Compound 13

Compound 12 (11.76 g, 16.11 mmol) was mixed with N,N-dimethylaminopyridine (11.79 g, 96.62 mmol) and dried over $P_2O_2$ under reduced pressure overnight. The dried mixture was dissolved in anhydrous $CH_2Cl_2$ (94 mL). The reaction mixture was cooled to −15° C. (dry ice/ethanol bath). To the chilled solution was added trifluoromethanesulfonic anhydride (6.59 mL, 32.22 mmol) as a solution in anhydrous $CH_2Cl_2$ (70 mL). After stirring at −15 to −10° C. for 1.5 h under argon atmosphere, mixture was diluted with ice cold $CH_2Cl_2$ (200 mL). Washed the resulting solution with ice-cold saturated aqueous $NaHCO_3$ (200 mL) and brine (200 mL). The organic phase dried over anhydrous $Na_2SO_4$, filtered, and evaporated to a pale yellow oil. Purification by silica gel chromatography (1:1 hexanes:ethyl acetate) yielded Compound 13 (8.26 g, 59.5%) as a white foam. $^1$H NMR (300 MHz, $CDCl_3$) δ 8.19 (s, 1H), 7.85-7.78 (m, 4H), 7.56-7.21 (m, 14H), 6.36 (d, J=3.6 Hz, 1H), 5.57 (m, 1H), 5.50 (br s, 1H), 4.98 (d, J=11.9 Hz, 1H), 4.70-4.56 (m, 3H), 4.40 (d, J=11.1 Hz, 1H), 3.81 (d, J=10.6 Hz, 1H) 3.66 (d, J=11.1 Hz, 1H), 2.87 (s, 3H), 0.89 (s, 9H); $^{19}$F NMR (282 MHz, $CDCl_3$) δ−74.22; HRMS (TOF MS ES) Calcd for $C_{39}H_{41}F_3N_2O_{11}S_2Si\ Na^-$ 885.1771, found 885.1769; MS (ES) m/z 863.0 [M+H]$^+$.

l) Preparation of Compound 14

N,N-diisopropylethylamine (15.66 mL, 89.90 mmol) and N-methoxy amine (4.23 g, 90 mmol) were added to Compound 13 (7.86 g, 9.12 mmol) dissolved in anhydrous DMF (12 mL) in a pressure bottle. The reaction mixture was heated at 60° C. for 18 h. The reaction mixture was poured into ethyl acetate (300 mL) and washed sequentially with aqueous $NaHCO_3$ (5 wt %, 2×300 mL) and brine (300 mL). The organic phase was dried over anhydrous $Na_2SO_4$, filtered, and evaporated. The residue obtained was purified by silica gel chromatography (1:1 hexanes:EtOAc) to yield Compound 14 (5.09 g, 85% yield) as a white foam. $^1$H NMR (300 MHz, DMSO-$d_4$) δ 11.39 (s, 1H), 7.93-7.81 (m, 4H), 7.73-7.32 (m, 14H), 5.98 (br s, 1H), 5.15 (d, J=8.1 Hz, 1H), 4.86-4.69 (m, 2H), 4.31 (s, 1H), 4.17 (s, 1H), 3.96-3.86 (m, 2H), 3.53 (s, 3H), 3.47 (d, J=11.9 Hz, 1H) 2.94 (br s, 1H), 0.95 (s, 9H); HRMS (TOF MS ES) Calcd for $C_{38}H_{41}N_3O_6Si\ Na^+$ 686.2662, found 686.2657; MS (ES) m/z 664.2 [M+H]$^+$.

m) Preparation of Compound 15

To a solution of Compound 14 (4.98 g, 7.5 mmol) in dichloromethane (77 mL) water (0.3 mL, 16.54 mmol) and 2,4-dichloro-5,6-dicyano-1,4-benzoquinone (9.76 g, 43 mmol) were added. The dark brown solution was stirred at room temperature for 18 h. The reaction mixture was diluted with ethyl acetate (200 mL) and washed sequentially with aqueous $NaHCO_3$ (5 wt %, 2×200 mL) and brine (200 mL). The organic phase was dried over anhydrous $Na_2SO_4$, filtered, and evaporated. The residue obtained was purified by silica gel column chromatography and eluted with 5% MeOH and 0.5% triethyl amine in $CH_2Cl$ to yield Compound 15 (3.36 g, 85.5% yield) as a white foam. $^1$H NMR (300 MHz, DMSO-$d_6$) δ 11.37 (s, 1H), 7.79 (d, J=8.9 Hz, 1H), 7.70-7.42 (m, 10H), 5.95 (br s, 1H), 5.61 (d, J=3.8 Hz, 1H), 5.29 (d, J=8.1 Hz, 1H), 4.09 (br s, 1H), 3.89 (br s, 2H), 3.85 (s, 1H), 3.49 (s, 3H), 3.43 (d, J=11.7 Hz, 1H) 2.83 (br s, 1H), 1.03 (s, 9H); $^{13}$C NMR (75 MHz, $CD_3OD$) δ 166.4, 151.8, 141.8, 137.0, 136.7, 134.4, 133.9, 131.3, 129.2, 101.8, 89.9, 83.5, 71.7, 68.5, 61.3, 61.2, 54.9, 27.5, 20.3; HRMS (TOF MS ES) Calcd for $C_{27}H_{33}N_3O_6Si\ Na^+$ 546.2036, found 546.2029; MS (ES) m/z 524.1 [M+H]$^+$.

n) Preparation of Compound 16

To a stirred solution of Compound 15 (3.30 g, 6.31 mmol) in THF (63 mL), triethylamine (2.18 mL, 15.66 mmol) and triethylamine trihydrofluoride (5.10 mL, 31.31 mmol) were added. The resulting reaction mixture was stirred at room temperature for 18 h. Solvent was removed under reduced pressure to get an oil and this oily residue was loaded on to a silica gel column and eluted with 5% MeOH and 1% triethylamine in $CH_2Cl_2$ to yield Compound 16 (1.53 g, 85%) as a white solid. $^1$H NMR (300 MHz, DMSO-$d_6$) δ 11.32 (s, 1H), 7.82 (d, J=7.9 Hz, 1H), 5.89 (br s, 1H), 5.62 (d, J=8.3 Hz, 1H), 5.45 (d, J=4.35 Hz, 1H), 5.09 (t, J=5.5 Hz, 18H), 3.93 (br s, 1H), 3.79 (s, 1H), 3.70-3.57 (m, 2H), 3.48 (s, 3H), 3.41 (d, J=11.7 Hz, 1H), 2.78 (br s, 1H); $^{13}$C NMR (75 MHz, $CD_3OD$) δ 166.6, 151.9, 141.9, 101.9, 90.1, 83.4, 71.7, 68.6, 61.2, 58.8; HRMS (TOF MS ES) Calcd for $CH_{11}H_{16}N_3O_6^+$ 286.1039, found 286.1046; MS (ES) m/z 286 [M+H]$^+$.

o) Preparation of Compound 17

Compound 16 (1.48 g, 5.19 mmol) was mixed with 4,4'-dimethoxytrityl chloride (2.50 g, 7.38 mmol) and dried over $P_2O_5$ under reduced pressure overnight. Dissolved the dried mixture in anhydrous pyridine (14 mL) and stirred the resulting solution at room temperature for 8 h under argon atmosphere. The reaction mixture was poured into $CH_2Cl_2$ (150 mL) and washed sequentially with aqueous $NaHCO_3$ (5 wt %, 150 mL) and brine (150 mL). The organic phase was dried over anhydrous $Na_2SO_4$, filtered, and evaporated. The residue obtained was purified by silica gel column chromatography and eluted with 0-5% MeOH in $CH_2Cl_2$ containing 1% triethylamine to yield Compound 17 (3.02 g, 99% yield) as a white foam. $^1$H NMR (300 MHz, DMSO-$d_6$) δ 11.38 (s, 1H), 7.81 (d, 8.1 Hz, 1H), 7.41-7.25 (m, 9H), 6.91 (d, J=8.5 Hz, 4H), 5.94 (br s, 1H), 5.59 (d, J=4.0 Hz, 1H), 5.41 (d, J=7.7 Hz, 1H) 4.15 (br s, 1H), 3.84 (s, 1H), 3.75 (s, 6H), 3.48 (s, 3H), 3.40-3.29 (m, 2H), 3.21 (d, J=10.7 Hz, 1H), 2.87 (br s, 1H); $^{13}$C NMR (75 MHz, $CD_3OD$) δ 166.5, 160.4, 151.7, 150.2, 146.3, 141.9, 137.1, 136.8, 131.5, 129.5, 129.0, 128.2, 114.4, 101.9, 88.9, 88.1, 83.6, 72.2, 68.4, 61.2, 60.5, 55.9; HRMS (TOF MS ES) Calcd for $C_{32}H_{32}N_3O_8^-$ 586.2189, found 586.2190; MS (ES) m/z 585.7 [M−H]$^-$.

p) Preparation of Compound 18

A mixture of Compound 17 (1.31 g, 2.22 mmol) and 1H-tetrazole (0.14 g, 2.00 mmol) was dried over $P_2O_5$ over night under reduced pressure. To the solution of the mixture in anhydrous DMF (5.44 mL), 2-cyanoethyl-N,N-diisopropylphosphorodiamidite (1.03 mL, 3.25 mmol) and 1-methylimidazole (0.052 mL, 0.65 mmol) were added. The reaction mixture was stirred at room temperature for 6 h under argon atmosphere. The reaction mixture was poured into ethyl acetate (50 mL) and the organic layer was washed with aqueous $NaHCO_3$ (5% by wt, 100 mL), brine (60 mL), dried ($Na_2SO_4$) and evaporated. The residue was purified by silica gel column chromatography (1:1 ethyl acetate/hexane) to yield Compound 18 (1.57 g, 89% yield) as a white foam. $^{31}$P NMR (121 MHz, $CDCl_3$) δ 148.57, 148.00; HRMS (FAB) Calcd for $C_{41}H_{51}N_5O_9P^+$ 788.3424, found 788.3428.

Example 2

Preparation of Compound 23 (Scheme 2)

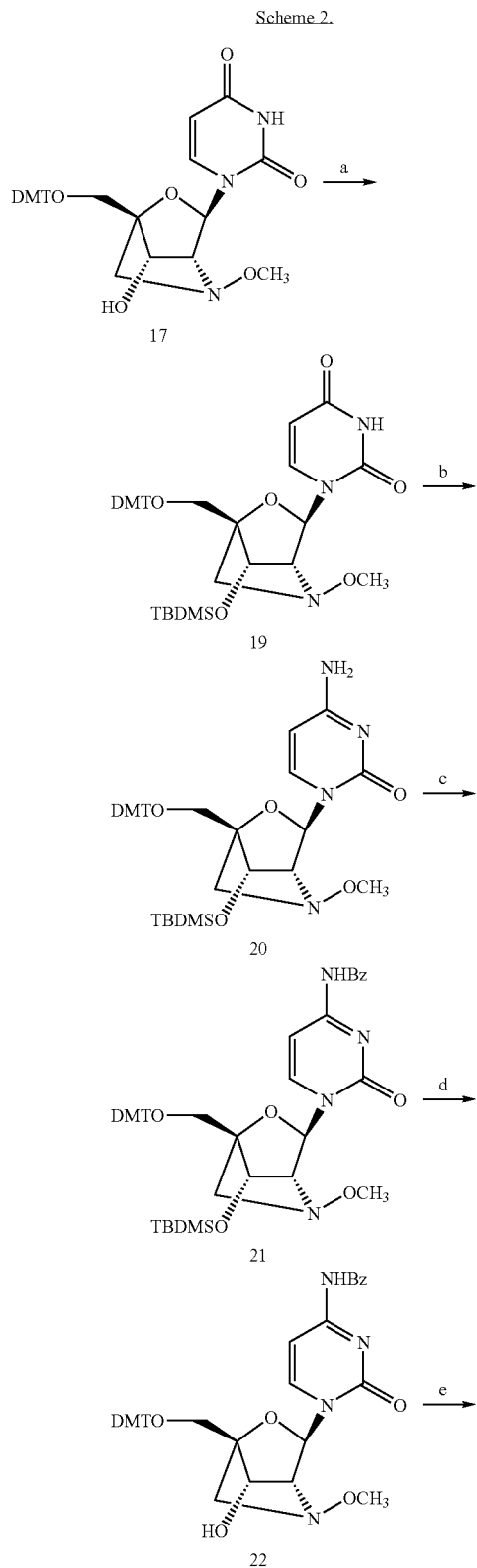

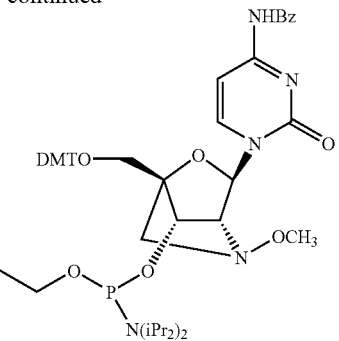

(a) DMF, imidazole, tert-butyldimethylsilyl chloride, rt, 86%; (b) i) 1,2,4-triazole, POCl$_3$, triethylamine, CH$_3$CN, 0° C. to rt, ii) aqueous ammoina, dioxane; (c) benzoic anhydride, DMF, rt, 98%; (d) triethyl amine, triethylamine trihydrofluoride, THF, rt, 86%; (e) 2-cyanoethyl-N,N-diisopropylphosphorodiamidite, N-methylimidazole, 1-H-tetrazole, DMF, 84%.

a) Preparation of Compound 19

To a solution of Compound 17 (1.4 g, 2.38 mmol) and imidazole (1.62 g, 23.8) in anhydrous DMF (5.3 mL), tert-butyldimethylsilyl chloride (1.79 g, 11.90 mmol) was added. The reaction mixture was stirred at room temperature for 24 h under argon atmosphere. The reaction was quenched with aqueous NaHCO$_3$ (60 mL) and extraction was performed with ethyl acetate (2×50 mL). The combined organic phase was washed with brine (100 mL) and dried over anhydrous Na$_2$SO$_4$. After evaporation, the residue was purified by silica gel column chromatography and eluted with 80% ethyl acetate in hexane to yield the Compound 19 (1.43 g, 85.4%) as a white foam. $^1$H NMR (300 MHz, DMSO-d$_6$) δ 11.39 (s, 1H), 7.89 (d, J=8.1 Hz, 1H), 7.39-7.251 (m, 9H), 6.91 (d, J=8.9 Hz, 4H), 5.92 (br s, 1H) 5.44 (d, J=8.3 Hz, 1H) 4.27 (s, 1H), 3.86 (s, 1H), 3.74 (s, 6H), 3.45 (s, 3H), 3.32-3.29 (m, 2H), 3.22 (d, J=11.7 Hz, 1H), 2.92 (br s, 1H) 0.71 (s, 9H), 0.03 (s, 3H), −0.06 (s, 3H); $^{13}$C NMR (75 MHz, CDCl$_3$) δ 163.7, 159.0, 149.9, 144.6, 140.4, 135.6, 135.5, 130.3, 128.3, 128.2, 127.3, 113.5, 101.7, 88.3, 86.8, 83.4, 71.7, 67.0, 61.0, 60.6, 58.9, 55.5, 25.7, 18.1, −4.6, −5.0; MS (ES) m/z 699.8 [M−H]$^-$.

b) Preparation of Compound 20

A suspension of 1,2,4-triazole (4.65 g, 67.27 mmol) in anhydrous CH$_3$CN (25.4 mL) was cooled in an ice bath for 5 to 10 min under an argon atmosphere. To this cold suspension, POCl$_3$ (1.47 mL, 60 mmol) was added slowly over 10 rain and stirring continued for an additional 5 min. Triethylamine (11.00 mL, 79.20 mmol) was added slowly over 30 min, keeping the bath temperature around 0-2° C. The reaction mixture was stirred at 0-2° C. for an additional 30 min. Compound 19 (1.39 g, 1.98 mmol) in anhydrous CH$_3$CN (12.7 mL) was added in one portion and stirred for 10 minutes and the reaction mixture was removed from the ice bath and stirred at room temperature for 4 h under argon atmosphere. The mixture was concentrated to one third of its volume, diluted with ethyl acetate (100 mL), and washed with water (2×100 mL) and brine (100 mL). The organic phase was dried over anhydrous Na$_2$SO$_4$ and concentrated under reduced pressure. The resulting residue was dissolved in a solution of aqueous NH$_3$ (12.7 mL, 28-30 wt %) and dioxane (30.5 mL). The reaction mixture was stirred at room temperature overnight in a pressure bottle. The solvent was removed in vacuum and the resulting residue was purified by flash silica gel column chromatography and eluted with 5% MeOH in CH$_2$Cl$_2$ to yield Compound 20 (1.32 g, 95%) as a white foam. MS (ES) m/z 699.9 [M–H]⁻, HRMS (TOF ES MS) Calcd for C₃₈H₄₉N₄O₇Si⁺ 701.3356, found 701.3356.

c) Preparation of Compound 21

Compound 20 (1.34 g, 1.91 mmol) was dissolved in anhydrous DMF (5 mL) and benzoic anhydride (0.65 g, 2.88 mmol) was added with stirring at room temperature for 18 h. The reaction mixture was diluted with ethyl acetate (100 mL). The resulting organic phase was washed with a saturated aqueous NaHCO₃ (2×100 mL) and brine (100 mL). The ethyl acetate layer was dried over anhydrous Na₂SO₄ and concentrated in vacuum. The residue obtained was purified by flash silica gel column chromatography and eluted with 80% ethyl acetate in hexane to yield Compound 21 (1.52 g, 99%) as a white foam. ¹H NMR (300 MHz, DMSO-d₆) δ 11.33 (s, 1H), 8.43 (d, J=7.5 Hz, 1H) 8.02 (d, J=7.7 Hz, 2H), 7.65-7.24 (m, 13H), 6.92 (d, J=8.7 Hz, 4H), 6.02 (br s, 1H), 4.31 (s, 1H), 3.98 (s, 1H), 3.76 (s, 6H), 3.50 (s, 3H), 3.39-3.25 (m, 3H), 2.96 (br s, 1H) 0.70 (s, 9H), –0.01 (s, 3H), –0.09 (s, 3H); ¹³C NMR (75 MHz, CD₃CN) δ 168.4, 164.0, 160.0, 155.4, 146.0, 145.6, 136.8, 136.6, 134.6, 134.0, 131.2, 130.7, 129.7, 129.6, 129.2, 129.0, 128.2, 114.3, 97.0, 88.9, 87.4, 84.6, 72.6, 67.2, 61.7, 61.3, 60.1, 56.0, 26.1, 18.6, –4.3, –4.7; MS (ES) m/z 802.9 [M–H]⁻.

d) Preparation of Compound 22

In a 100 mL round bottom flask, triethylamine trihydrofluoride (1.52 mL, 9.33 mmol) was dissolved in anhydrous THF (18.7 mL). Triethylamine (0.65 mL, 4.67 mmol) was added to this solution, and the mixture was quickly poured onto Compound 21 (1.5 g, 1.87 mmol). The resulting mixture was stirred at room temperature for 48 h. The reaction mixture was poured into ethyl acetate (50 mL). The organic phase was washed sequentially with water (50 mL), 5% aqueous NaHCO₃ (50 mL) and brine (50 mL). The ethyl acetate layer was dried over anhydrous Na₂SO₄ and concentrated in vacuum under reduced pressure. The residue obtained was purified by silica gel column chromatography and eluted with 50% ethyl acetate in hexane to afford Compound 22 (1.17 g, 86%) as a white foam. ¹H NMR (300 MHz, DMSO-d₆) δ 11.32 (s, 1H), 8.36 (d, J=7.4 Hz, 1H) 8.02 (d, J=8.1 Hz, 2H), 7.66-7.25 (m, 13H), 6.93 (d, J=8.9 Hz, 4H), 6.05 (br s, 1H), 5.61 (d, J=3.8 Hz, 1H), 4.20 (d, J=3.6 Hz, 1H), 3.96 (s, 1H), 3.77 (s, 6H), 3.53 (s, 3H), 3.43-3.23 (m, 3H), 2.90 (br s, 1H); ¹³C NMR (75 MHz, CD₃CN) δ 168.0, 163.7, 159.6, 155.3, 145.8, 145.5, 136.8, 136.5, 134.3, 133.7, 130.9, 130.8, 129.5, 129.0, 128.9, 128.8, 127.9, 114.0, 96.7, 88.4, 87.2, 84.0, 71.8, 67.1, 61.1, 60.8, 60.0, 55.8; MS (ES) m/z 691.2 [M+H]⁺, HRMS (TOF ES MS) Calcd for C₃₉H₃₈N₄O₈Na⁺ 713.2587, found 713.2573.

e) Preparation of Compound 23

A mixture of Compound 22 (1.08 g, 1.57 mmol) and 1H-tetrazole (0.1 g, 1.4 mmol) was dried over P₂O₅ over night under reduced pressure. To the solution of the mixture in anhydrous DMF (4.3 mL), 2-cyanoethyl-N,N-diisopropylphosphorodiamidite (0.75 mL, 2.35 mmol) and 1-methylimidazole (0.032 mL, 0.47 mmol) were added. The reaction mixture was stirred at room temperature for 6 h under argon atmosphere. The reaction mixture was poured into ethyl acetate (40 mL) and the organic layer was washed with aqueous NaHCO₃ (5 wt %, 100 mL), brine (50 mL), dried (Na₂SO₄) and evaporated. The residue obtained was purified by silica gel column chromatography (1:1 ethyl acetate/hexane) to yield Compound 23 (1.17 g, 84% yield) as a white foam. ³¹P NMR (121 MHz, CDCl₃) δ 149.91, 149.00; HRMS (TOF MS ES) Calcd for C₄₈H₅₆N₆O₆P⁺ 891.3846, found 891.3832.

Example 3

Preparation of Compound 34 (Scheme 3)

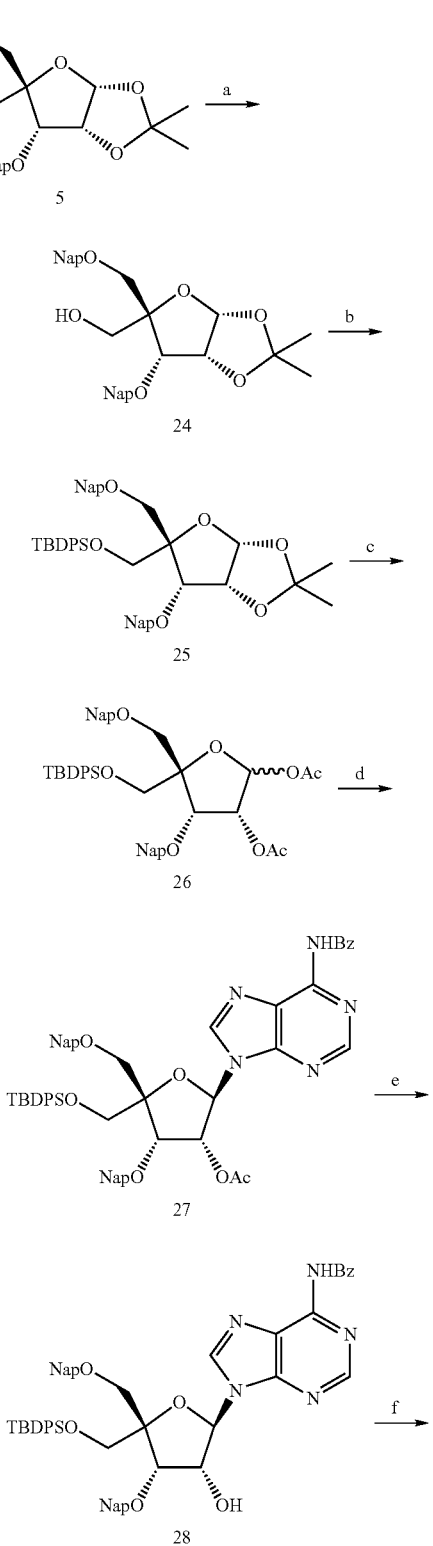

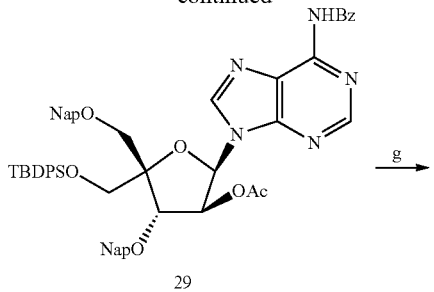

29

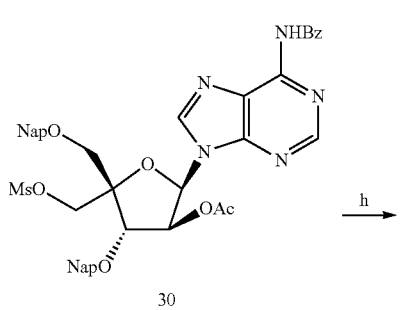

30

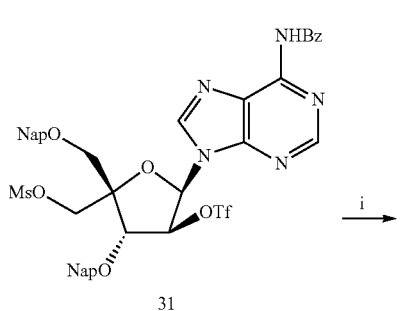

31

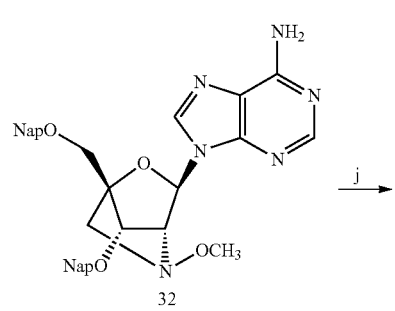

32

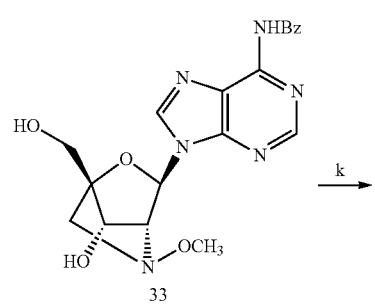

33

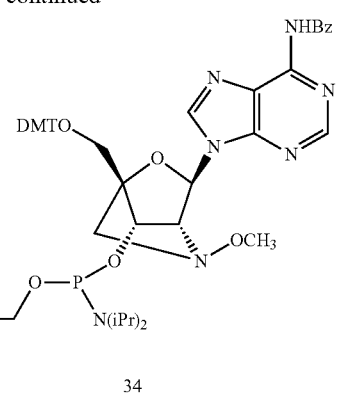

34

(a) NaH, DMF, 2-(bromomethyl)-naphthalene; (b) tert-butyldiphenysilyl chloride, imidazole, DMF; (c) Ac₂O, Ac₂OH, H₂SO₄; (d) 6-N-benzoyladenine, SnCl₄, CH₃CN, rt; (e) 7M NH₃ in MeOH, 0° C.; (f) i) Tf₂O, DMAP, CH₂Cl₂, -30 to -10° C. (i) N-methoxyamine, DMF, iPr₂NEt, 60° C. (j) i) benzoyl tetrazole, DMF, 40° C.; ii) DDQ, CH₂Cl₂, H₂O; (k) 2-cyanoethyl-N,N-diisopropylphosphorodiamidite, N-methylimidazole, 1-H-tetrazole, DMF.

Example 4

Preparation of Compound 42 (Scheme 4)

Scheme 4.

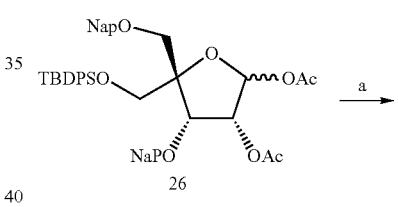

26

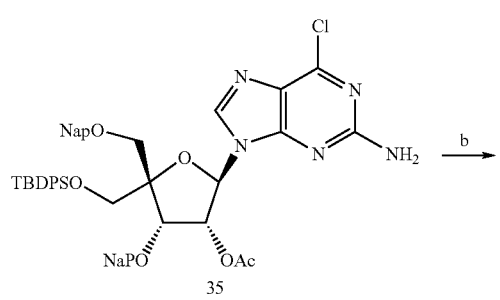

35

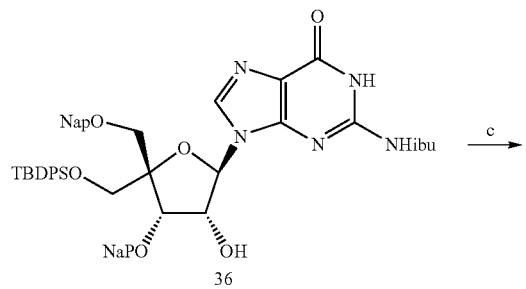

36

-continued

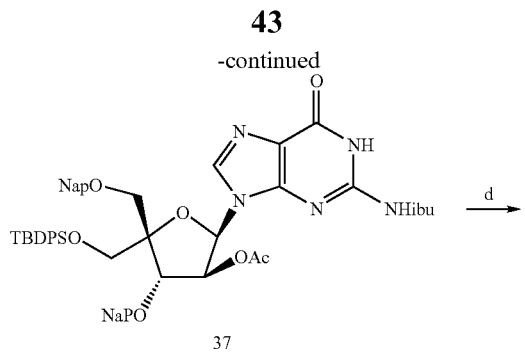

37

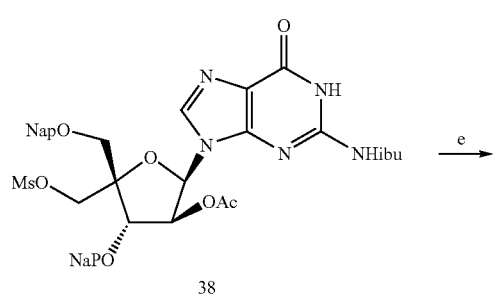

38

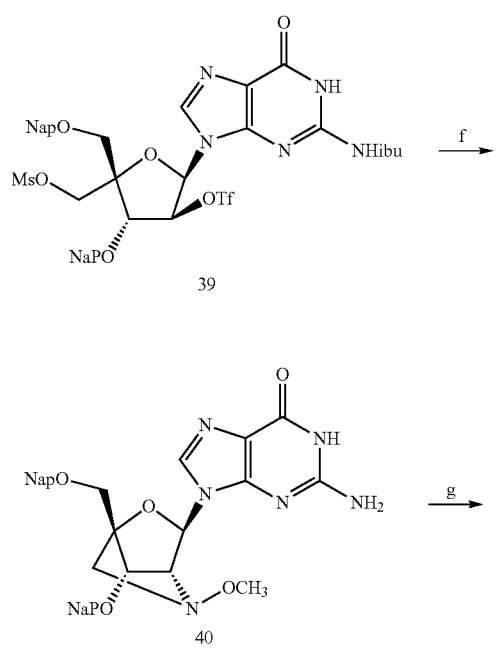

39

40

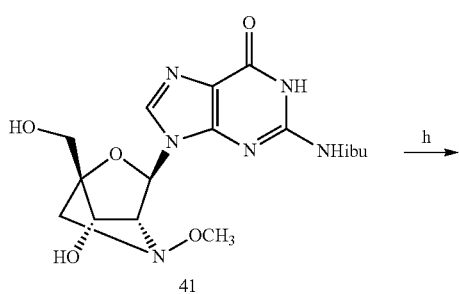

41

-continued

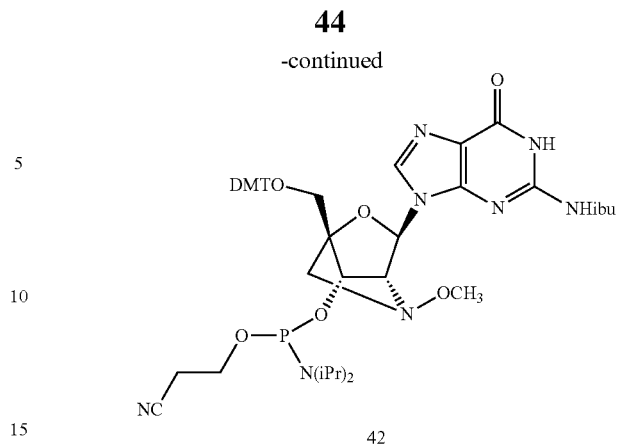

42

(a) 2-amino-6-chloropurine, N,O-bis(trimethylsilyl)acetamide, TMS-triflate, 1,2-dichloroethane; (b) i) HOCH₂CH₂CN, NaH ii) TMSCl, Pyridine, isobutyryl chloride, ammonia, H₂O; (c) i) Tf₂O, DMAP, CH₂Cl₂, -30 to -10° C. ii) KOAc, 18-crown-6, toluene, 80° C.; (d) i) TEA3HF, TEA, THF ii) MsCl, Et₃N, DMAP, CH₂Cl₂, rt; (e) i) 7M NH₃ in MeOH, 0° C. ii) Tf₂O, DMAP, CH₂Cl₂, -30 to -10° C. (f) N-methoxyamine, DMF, iPr₂NEt, 60° C. (g) Pyridine, isobutyryl chloride, rt; ii) DDQ, CH₂Cl₂, H₂O; (g) 2-cyanoethyl-N,N-diisopropylphosphorodiamidite, N-methylimidazole, 1-H-tetrazole, DMF.

Example 5

Preparation of Compound 45 (Scheme 5)

Scheme 5.

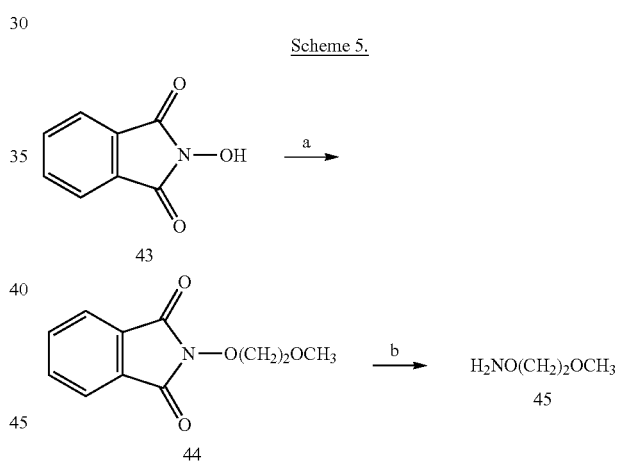

Step a DBU, CH₃CN, (2-methoxy)ethylbromide, rt; step b N-methylhydrazene, CH₂Cl₂, -10° C.

a) Preparation of Compound 44

Compound 43 (13.15 g, 96.60 mmol) was dissolved in anhydrous acetonitrile (40 mL) and 1,8-diazabicyclo[5.4.0]undec-7-ene (21.7 mL, 145.00 mmol) was added. After 5 minutes 2-(bromo)ethyl methyl ether (13.63 mL, 145 mmol) was added and the reaction mixture was stirred at room temperature for 18 hours. The solvent was removed under reduced pressure and the residue obtained was purified by silica gel column chromatography by elating with 30% ethyl acetate in hexane to yield compound 44 (10.23 g, 48,%) as a white solid. $^1$H NMR (300 MHz, CDCl₃) δ: 7.86-7.73 (m, 4H), 4.37 (m, 2H), 4.76 (m, 2H), 3.39 (s, 3H); $^{13}$C NMR (75 MHz, CDCl₃) δ: 163.6, 134.6, 129.1, 123.6, 77.2, 70.6, 59.2; ES MS m/z 222.0 [M+H]⁻.

b) Preparation of Compound 45

Compound 44 (9.2 g, 41.60 mmol) was dissolved in CH₂Cl₂ (100 mL) with cooling to −10° C. and N-methylhydrazine (2.94 mL, 55.20 mmol) was added with stirring for 2 hours with the temperature maintained at −10° C. The precipitate formed was filtered and the solvent was concentrated under reduced pressure to yield compound 45 (2.93 g, 77%) as a colorless oil. $^1$H NMR (300 MHz, CDCl$_3$) δ: 3.83 (min, 2H), 3.57 (m, 2H), 3.39 (s, 3H); $^{13}$C NMR (75 MHz, CDCl$_3$) δ: 74.5, 70.7, 59.3.

Example 6

Preparation of Compound (Scheme 6)

Scheme 6.

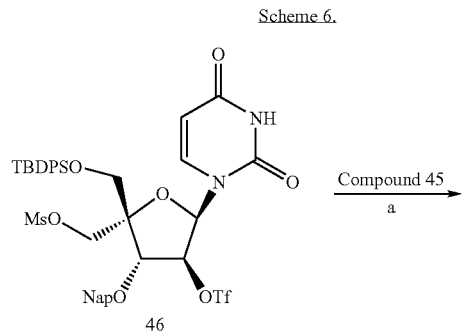
46

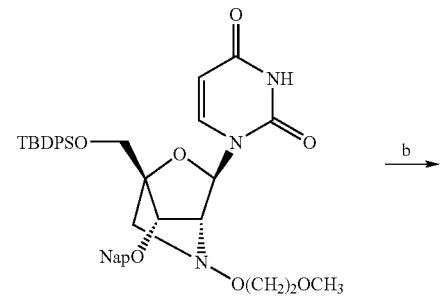
47

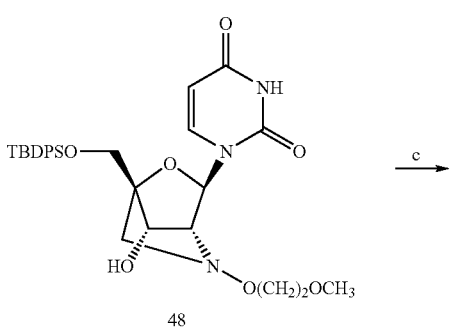
48

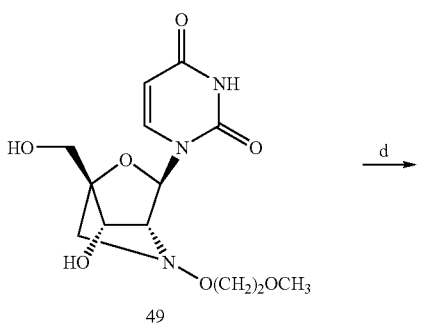
49

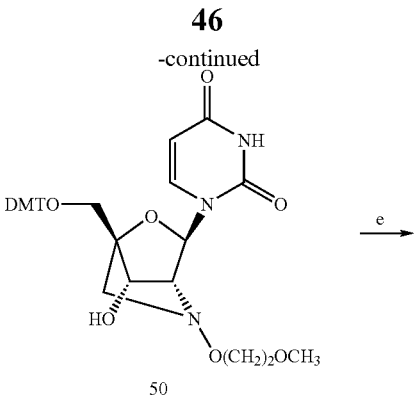
50

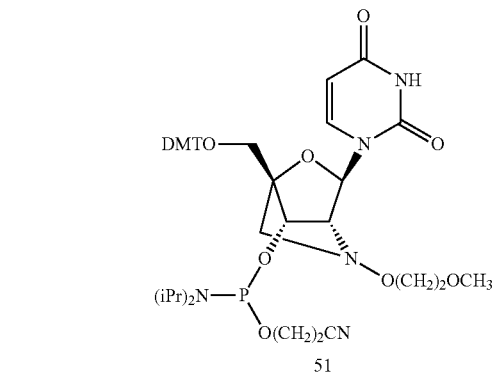
51

(a) N-(2-methoxy)ethoxyamine 3, DMA, iPr$_2$NEt, 60° C., 18 h, 64%;
(b) DDQ, CH$_2$Cl$_2$, H$_2$O, 18 h, rt, 98%; (c) TEA•3HF, TEA, THF, 92%; (d) DMTCl, Py, rt, 90%; (e) 2-cyanoethyl-N,N-diisopropylphosphorodiamidite, N-methylimidazole, 1-H tetrazole, DMF, 82%.

a) Preparation of Compound 47

N,N-diisopropylethylamine (4.02 mL, 23.20 mmol) and N-(2-methoxy)ethoxyamine (Compound 45, 2.11 g, 23.20 mmol) were added to Compound 46 (2.00 g, 2.32 mmol) dissolved in anhydrous N,N-dimethylacetamide (DMA, 3.3 mL) in a pressure bottle. The reaction mixture was heated at 60° C. for 18 hours and poured into ethyl acetate (50 mL) and washed sequentially with aqueous NaHCO$_3$ (5 wt %, 2×50 mL) and brine (50 mL). The organic phase was dried over anhydrous Na$_2$SO$_4$, filtered and evaporated. The residue obtained was purified by silica gel chromatography (1:1 hexanes:EtOAc) to yield compound 47 (1.04 g, 64% yield) as a foam. $^1$H NMR (300 MHz, DMSO-d$_6$) δ 11.38 (s, 1H), 7.93-7.81 (m, 4H), 7.72 (d, J=8.2 hz, 1H), 7.62-7.31 (m, 14H), 5.98 (br s, 1H), 5.16 (d, J=8.0 Hz, 1H), 4.86-4.68 (m, 2H), 4.26 (s, 1H), 4.16 (s, 1H), 3.96-3.76 (m, 4H), 3.66-3.40 (m, 3H), 3.26 (s, 3H), 3.0 (br s, 1H), 0.95 as, 9H); MS (ES) m/z 708.3 [M+H]$^+$.

b) Preparation of Compound 48

To a solution of Compound 47 (0.6 g, 0.85 mmol) in dichloromethane (9.2 mL) was added water (0.04 mL, 2.22 mmol) and 2,4-dichloro-5,6-dicyano-1,4-benzoquinone (1.11 g, 4.87 mmol). The dark brown solution was stirred at room temperature for 18 hours, diluted with ethyl acetate (60 mL) and washed sequentially with aqueous NaHCO$_3$ (5 wt %, 2×60 mL) and brine (50 mL). The organic phase was dried over a hydrons Na$_2$SO$_4$, filtered, and evaporated. The residue obtained was purified by silica gel column chromatography by eluting with 5% MeOH and 0.5% triethylamine in CH$_2$Cl$_2$ to yield Compound 48 (0.47 g, 98% yield) as a white foam. $^1$H NMR (300 MHz, DMSO-$d_6$) δ 11.38 (s, 1H), 7.79 (d, J=8.1 Hz, 1H), 7.70-7.60 (m, 4H), 7.48-7.41 (m, 6H), 5.97 (br s, 1H), 5.60 (d, J=4.1 Hz, 1H), 5.29 (d, J=8.0 Hz, 1H), 4.08 (d, J=4.0 Hz, 1H), 3.89 (br s, 2H), 3.81-3.74 (m, 3H), 3.63-3.42 (m, 3H), 3.28 (s, 3H) 2.91 (br s, 1H), 1.04 (s, 9H); MS (ES) m/z 568.2 [M+H]$^+$.

c) Preparation of Compound 49

To a stirred solution of Compound 48 (0.46 g, 0.82 mmol) in THF (63 mL) was added triethylamine (0.28 mL, 2.03 mmol) and triethylamine trihydrofluoride (0.66 mL, 4.05 mmol). The resulting reaction mixture was stirred at room temperature for 18 hours and evaporated under reduced pressure to get an oil. The oil was loaded on to a silica gel column and eluted with 5% MeOH and 1% triethylamine in $CH_2Cl_2$ to yield Compound 49 (0.26 g, 99%) as a white solid. $^1$H NMR (300 MHz, DMSO-$d_6$) δ 11.29 (s, 1H), 7.82 (d, J=8.1 Hz, 1H), 5.90 (br s, 1H), 5.61 (d, J=8.1 Hz, 1H), 5.44 (br s, 1H), 5.09 (br s, 1H), 3.93 (br s, 1H), 3.83-3.72 (m, 3H), 3.64 (d, J=4.1 Hz, 2H), 3.58-3.39 (m, 3H), 3.31 (s, 3H), 2.85 (br s, 1H); MS (ES) m/z 330.1 [M+H]$^+$.

d) Preparation of Compound 50

Compound 49 (0.21 g, 0.64 mmol) was and 4,4'-dimethoxytrityl chloride (0.31 g, 0.92 mmol) were dried over $P_2O_5$ under reduced pressure overnight and then dissolved in anhydrous pyridine (1.8 mL) with stirring at room temperature for 6 hours under argon atmosphere. The reaction mixture was poured into $CH_2Cl_2$ (30 mL) and washed sequentially with aqueous NaHCO$_3$ (5 wt %, 30 mL) and brine (30 mL). The organic phase was dried over anhydrous $Na_2SO_4$, filtered, and evaporated. The resulting residue was purified by silica gel column chromatography by eluting with 0-5% MeOH in $CH_2Cl_2$ containing 1% triethylamine to yield Compound 50 (0.36 g, 90% yield) as a foam. $^1$H NMR (300 MHz, DMSO-$d_6$) δ 11.36 (s, 1H), 7.81 (d. J=8.1 Hz, 1H), 7.51-7.12 (m, 9H), 6.91 (d, J=8.5 Hz, 4H), 5.95 (br s, 1H), 5.57 (d, J=4.4 Hz, 1H), 5.41 (d, J=8.1 Hz, 1H) 4.13 (br s, 1H), 3.81-3.78 (m, 3H), 3.75 (s, 6H), 3.58-3.43 (m, 2H), 3.40-3.20 (m, 3H), 3.26 (s, 3H), 2.87 (br s, 1H); MS (ES) m/z 632.2 [M+H]$^+$.

e) Preparation of Compound 51

A mixture of Compound 50 (0.12 g, 0.19 mmol) and 1H-tetrazole (0.012 g, 0.17 mmol) was dried over $P_2O_5$ over night under reduced pressure. The dried mixture was dissolved in anhydrous DMF (0.53 mL) and 2-cyanoethyl-N,N-diisopropylphosphorodiamidite (0.09 mL, 0.29 mmol) and 1-methylimidazole (0.005 mL, 0.06 mmol) were added. The reaction mixture was stirred at room temperature for 6 hours under an argon atmosphere. The reaction mixture was poured into ethyl acetate (30 mL) and the organic layer was washed with aqueous NaHCO$_3$ (5% by wt, 30 mL), brine (30 mL), dried (Na$_2$SO$_4$) and evaporated. The residue was purified by silica gel column chromatography (1:1 ethyl acetate/hexane) to yield Compound 51 (0.13 g, 82% yield) as a white foam. $^{31}$P NMR (121 MHz, CDCl$_3$) δ 149.10, 148.10; MS (FAB) m/z 832.4 [M−H]$^+$.

Example 7

Preparation of Compound 55 (Scheme 7)

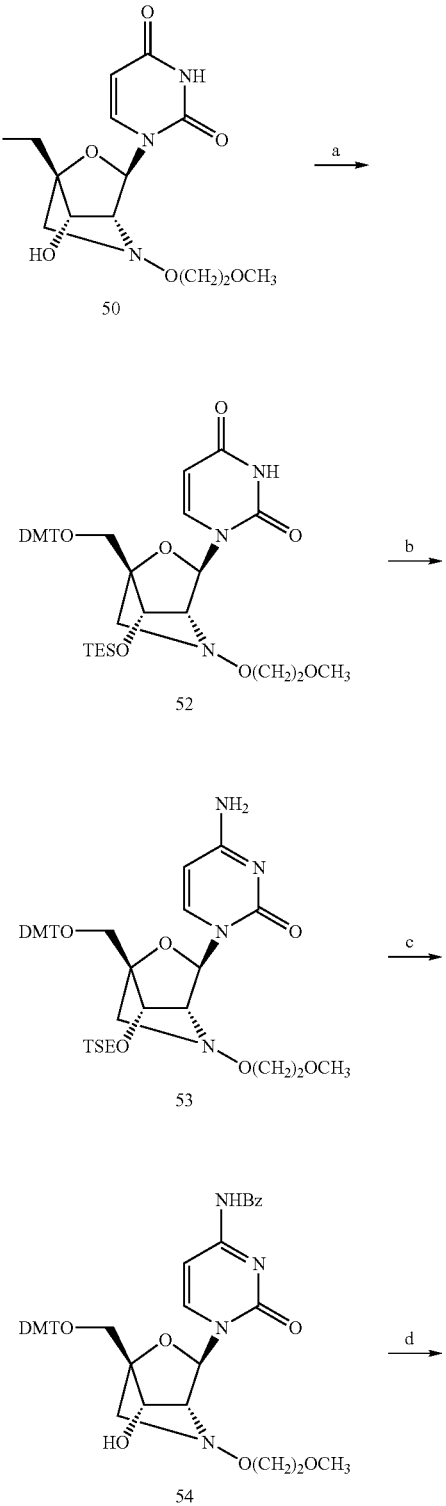

-continued

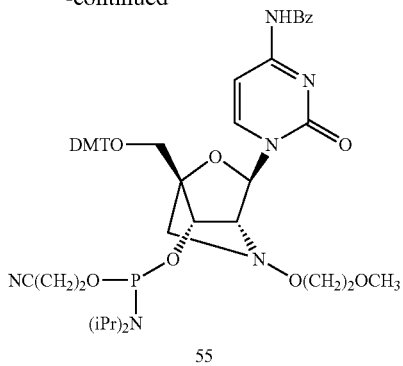

55

(a) DMF, imidazole, triethylsilyl chloride, rt, 92%;
(b) i) 1,2,4-triazole, POCl₃, triethylamine, CH₃CN, 0° C. to rt,
ii) aqueous NH₃, dioxane; (c) benzoic anhydride, DMF, rt, 98%;
(d) triethylamine, triethylamine trihydrofluoride, THF, rt, 82%;
(e) 2-cyanoethyl-N,N-diisopropylphosphorodiamidite, N-methylimidazole, 1-H-tetrazole, DMF.

a) Preparation of Compound 52

To a solution of Compound 50 (0.15 g, 0.24 mmol) and imidazole (0.07 g, 0.96) in anhydrous DMF (0.6 mL) was added triethylsilyl dichloride (0.08 mL, 0.48 mmol) and the mixture was at room temperature for 6 hours under an argon atmosphere. The reaction mixture was quenched with aqueous NaHCO₃ (20 mL) and extracted with ethyl acetate (2×200 mL). The combined organic phase was washed with brine (200 mL) and dried over anhydrous Na₂SO₄. After evaporation, the residue was purified by silica gel column chromatography and eluted with 0-5% MeOH and 1% triethylamine in CH₂Cl₂ to yield the Compound 52 (0.17 g, 92.%) as a white foam. ¹H NMR (300 MHz, DMSO-d₆) δ 11.36 (s, 1H), 7.90 (d, J=8.1 Hz, 1H), 7.50-7.11 (m, 9H), 6.90 (d, J=10.3 Hz, 4H), 5.96 (br s, 1H), 5.45 (d, J=8.1 Hz, 1H) 4.25 (s, 1H), 3.83 (s, 1H), 3.81-3.74 (m, 2H), 3.74 (s, 6H), 3.55-3.42 (m, 2H), 3.40-3.20 (m, 3H), 3.25 (s, 3H), 2.89 (br s, 1H), 0.89-0.76 (m, 9H), 0.60-0.31 (m, 6H); MS (ES) m/z 746.3 [M+H]⁺.

b) Preparation of Compound 53

A suspension of 1,2,4-triazole (0.64 g, 9.27 mmol) in anhydrous CH₃CN (3.6 mL) was cooled in an ice bath for 5 to 10 minutes under an argon atmosphere. To this cold suspension, POCl₃ (0.20 mL, 2.16 mmol) was added slowly with continued stirring for an additional 15 minutes. Triethylamine (1.51 mL, 10.84 mmol) was added slowly with the reaction mixture maintained at 0-2° C. with stirring for an additional 30 minutes following the addition. Compound 52 (0.20 g, 0.27 mmol) in anhydrous CH₃CN (1.8 mL) was added in one portion and stirred for 10 minutes with continued stirring under an argon atmosphere for 3 hours following removal of the ice bath. The mixture was diluted with ethyl acetate (30 mL), and washed with water (2×30 mL) and brine (30 mL). The organic phase was dried over anhydrous Na₂SO₄ and concentrated tinder reduced, pressure to provide a residue that was dissolved in a solution of aqueous NH₃ (1.55 mL, 28-30 wt %) and dioxane (3.9 mL). The solution was stirred at room temperature overnight in a pressure bottle. The solvent was removed under reduced vacuum and the resulting residue was purified by flash silica gel column chromatography (5% MeOH and 1% triethylamine in CH₂Cl₂) to yield Compound 53 (0.17 g, 82%) as a white foam. MS (ES) m/z 745.3 [M+H]⁺ c) Preparation of Compound 54

Compound 53 (0.16 g, 0.22 mmol) was dissolved in anhydrous DMF (0.6 mL) and benzoic anhydride (0.08 g, 0.35 mmol) was added with stirring at room temperature for 18 hours. The mixture was diluted with ethyl acetate (40 mL) and washed with a saturated aqueous NaHCO₃ (2×30 mL) and brine (30 mL). The ethyl acetate layer was dried over anhydrous Na₂SO₄ and concentrated under reduced pressure. To the residue a solution of triethylamine trihydrofluoride (0.18 mL, 1.08 mmol) and triethylamine (0.08 mL, 0.57 mmol) in anhydrous THF (2.2 mL) was added. The resulting mixture was stirred at room temperature for 2 hours and poured into ethyl acetate (30 mL). The organic phase was washed sequentially with water (30 mL), 5% aqueous NaHCO₃ (30 mL) and brine (30 mL). The ethyl acetate layer was dried over anhydrous Na₂SO₄ and concentrated under reduced pressure. The residue obtained was purified by silica gel column chromatography (5% MeOH and 1% triethylamine in CH₂Cl₂) to afford Compound 54 (0.14 g, 89%) as a foam. ¹H NMR (300 MHz, DMSO-d₆) δ 11.31 (s, 1H), 8.36 (d, J=7.5 Hz, 1H) 8.02 (d, J=8.7 Hz, 2H), 7.87 (d, J=9.7 Hz, 1H), 7.66-7.26 (m, 13H), 6.94 (d, J=8.9 Hz, 4H), 6.03 (br s, 1H), 5.59 (d, J=4.4 Hz, 1H), 4.18 (d, J=4.4 Hz, 1H), 3.92 (s, 1H), 3.86-3.68 9 m, 2H), 3.77 (s, 6H), 3.61-3.47 (m, 2H), 3.45-3.23 (m, 2H), 3.27 (s, 3H), 2.94 (br s, 1H); MS (ES) m/z 735.3 [M+H]⁺.

d) Preparation of Compound 55

A mixture of Compound 54 (0.13 g, 0.17 mmol) and 1H-tetrazole (0.01 g, 0.15 mmol) was dried over night under reduced pressure over P₂O₅. The dried mixture was dissolved in anhydrous DMF (0.5 mL) and 2-cyanoethyl-N,N-diisopropylphosphorodiamidite (0.08 mL, 0.26 mmol) and 1-methylimidazole (0.004 mL, 0.05 mmol) were added. The reaction mixture was stirred at room temperature for 6 hours under an argon atmosphere. The reaction mixture was poured into ethyl acetate (20 mL) and the organic layer was washed with aqueous NaHCO₃ (5 wt %, 20 mL), brine (20 mL), dried (Na₂SO₄) and concentrated under reduced pressure. The crude material is being purified.

Example 8

Preparation of Compound 58 (Scheme 8)

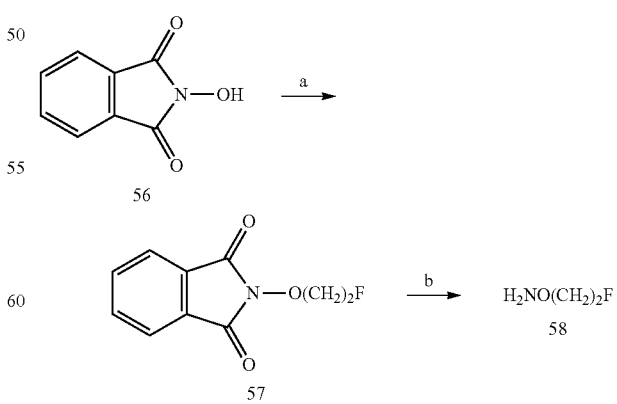

(a) Ph₃P, THF, (2-fluoro)ethanol, DEAD, rt; (b) N-methylhydrazene, CH₂Cl₂, -10° C.

Example 9
Preparation of Compound 63 (Scheme 9)
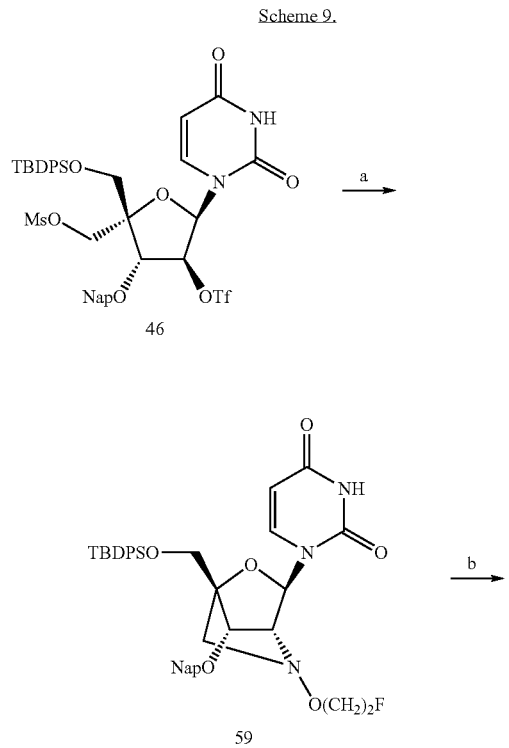
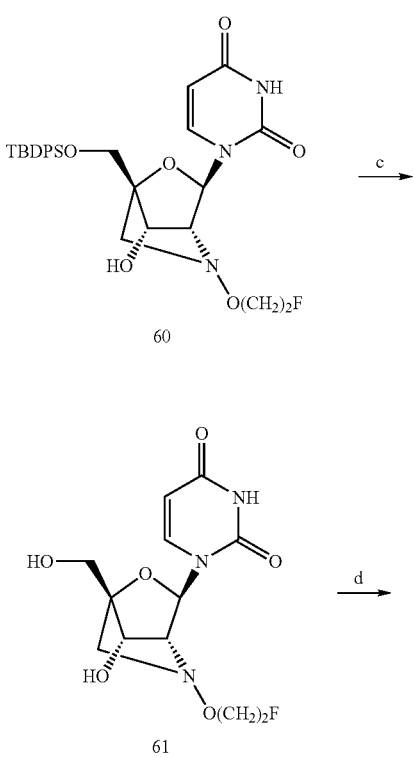
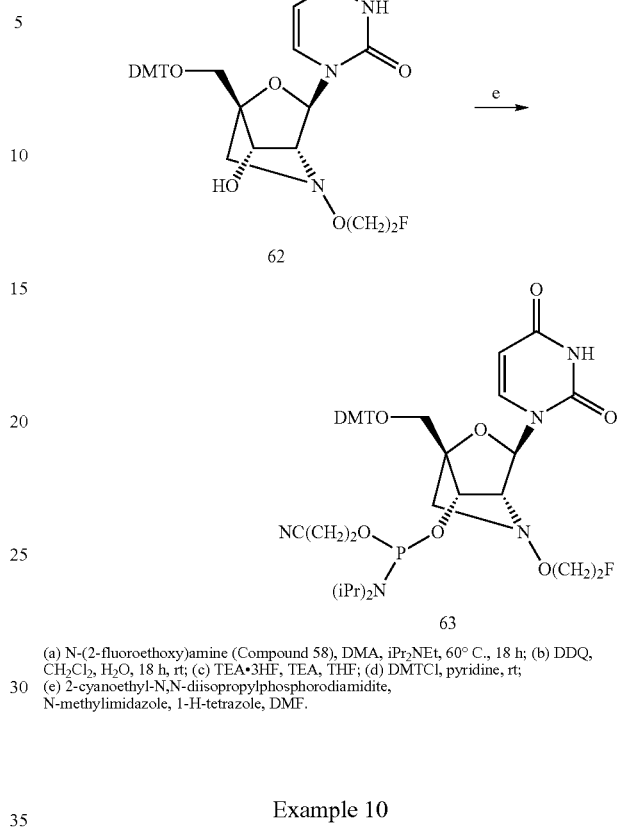
(a) N-(2-fluoroethoxy)amine (Compound 58), DMA, iPr₂NEt, 60° C., 18 h; (b) DDQ, CH₂Cl₂, H₂O, 18 h, rt; (c) TEA·3HF, TEA, THF; (d) DMTCl, pyridine, rt; (e) 2-cyanoethyl-N,N-diisopropylphosphorodiamidite, N-methylimidazole, 1-H-tetrazole, DMF.
Example 10
Preparation of Compound 68 (Scheme 10)
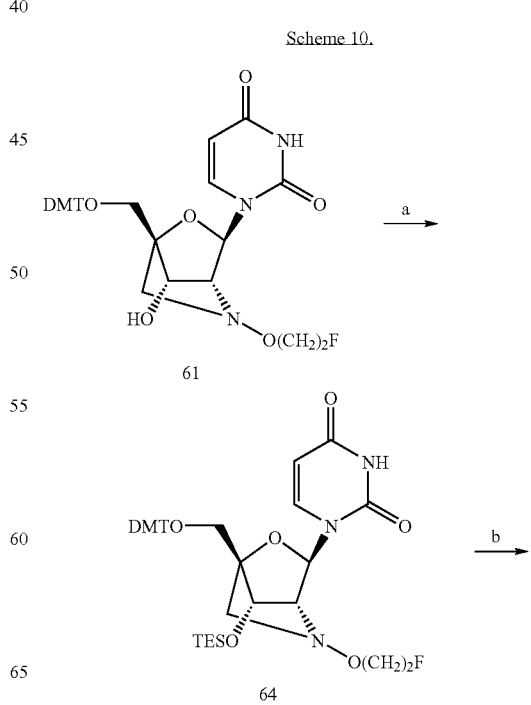

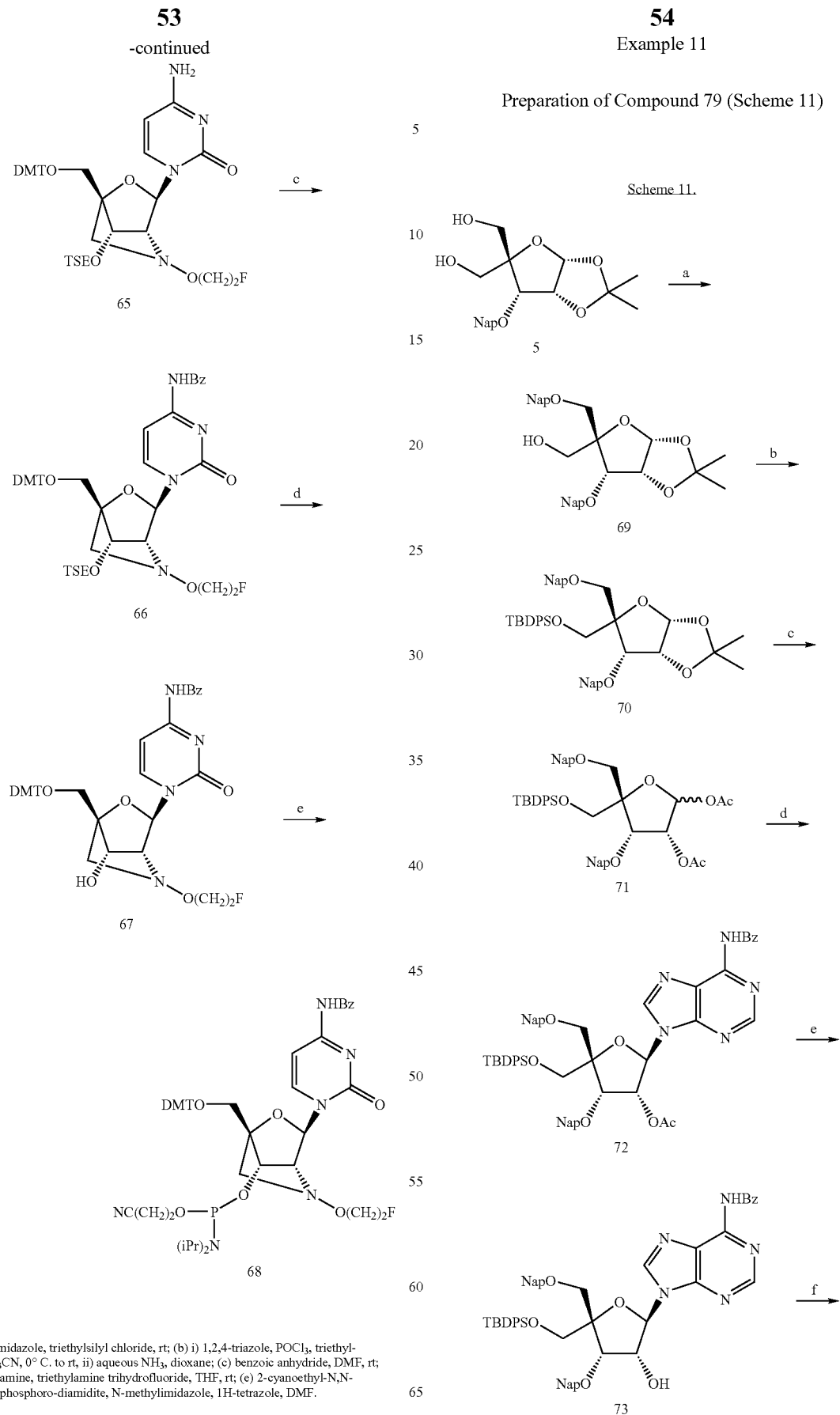
Example 11
Preparation of Compound 79 (Scheme 11)
(a) DMF, imidazole, triethylsilyl chloride, rt; (b) i) 1,2,4-triazole, POCl$_3$, triethylamine, CH$_3$CN, 0° C. to rt, ii) aqueous NH$_3$, dioxane; (c) benzoic anhydride, DMF, rt; (d) triethyl amine, triethylamine trihydrofluoride, THF, rt; (e) 2-cyanoethyl-N,N-diisopropylphosphoro-diamidite, N-methylimidazole, 1H-tetrazole, DMF.

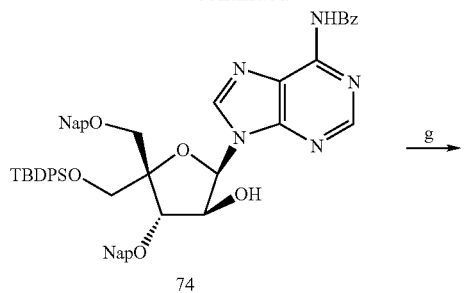

74

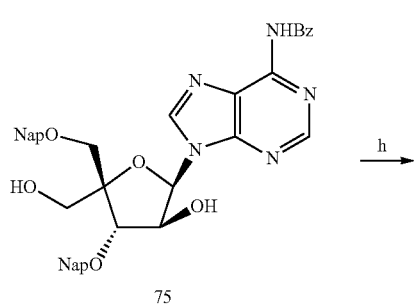

75

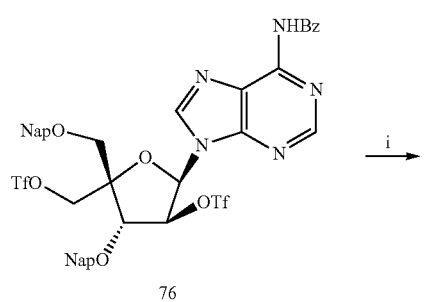

76

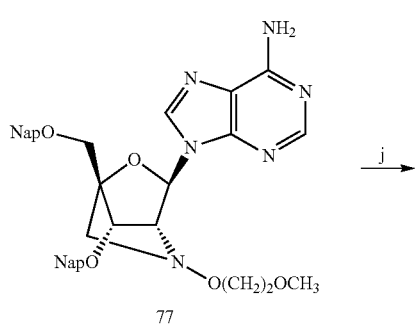

77

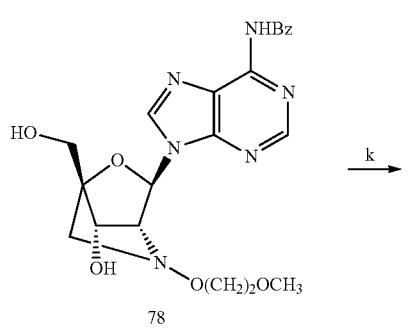

78

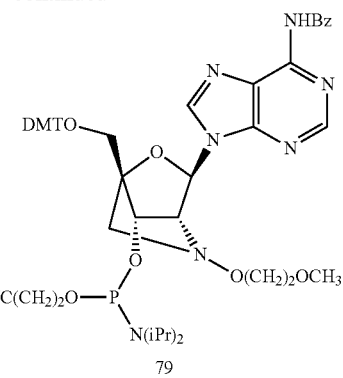

79

(a) NaH, DMF, 2-(bromomethyl)-naphthalene; (b) tert-butyldiphenylsilyl chloride, imidazole, DMF; (c) Ac₂O, Ac₂OH, H₂SO₄; (d) 6-N-benzoyladenine, SnCl₄, CH₃CN, rt; (e) 7M NH₃ in MeOH, 0° C.; (f) i) DMSO, oxalyl chloride, TEA, -78° C. ii) NaBH₄; (g) i) TEA·3HF, TEA, THF (h) Tf₂O, DMAP, CH₂Cl₂, -30 to -10° C., (i) N-(2-methoxy)ethoxyamine 3, DMF, iPr₂NEt, 60° C. (j) i) benzoyl tetrazole, DMF, 40° C.; ii) DDQ, CH₂Cl₂, H₂O; (k) i) DMTCl, pyridine, rt, ii) 2-cyanoethyl-N,N-diisopropylphosphorodiamidite, N-methylimidazole, 1-H-tetrazole, DMF.

Example 12

Preparation of Compound 87 (Scheme 12)

Scheme 12.

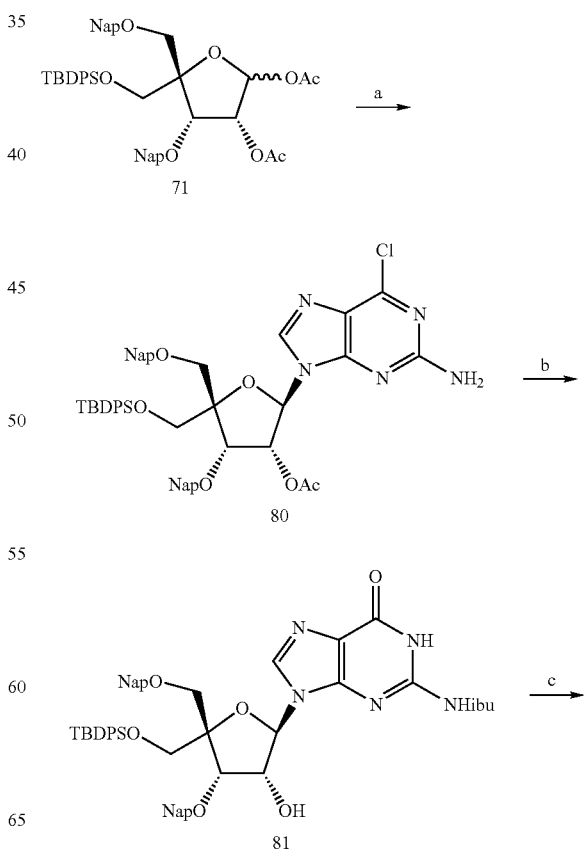

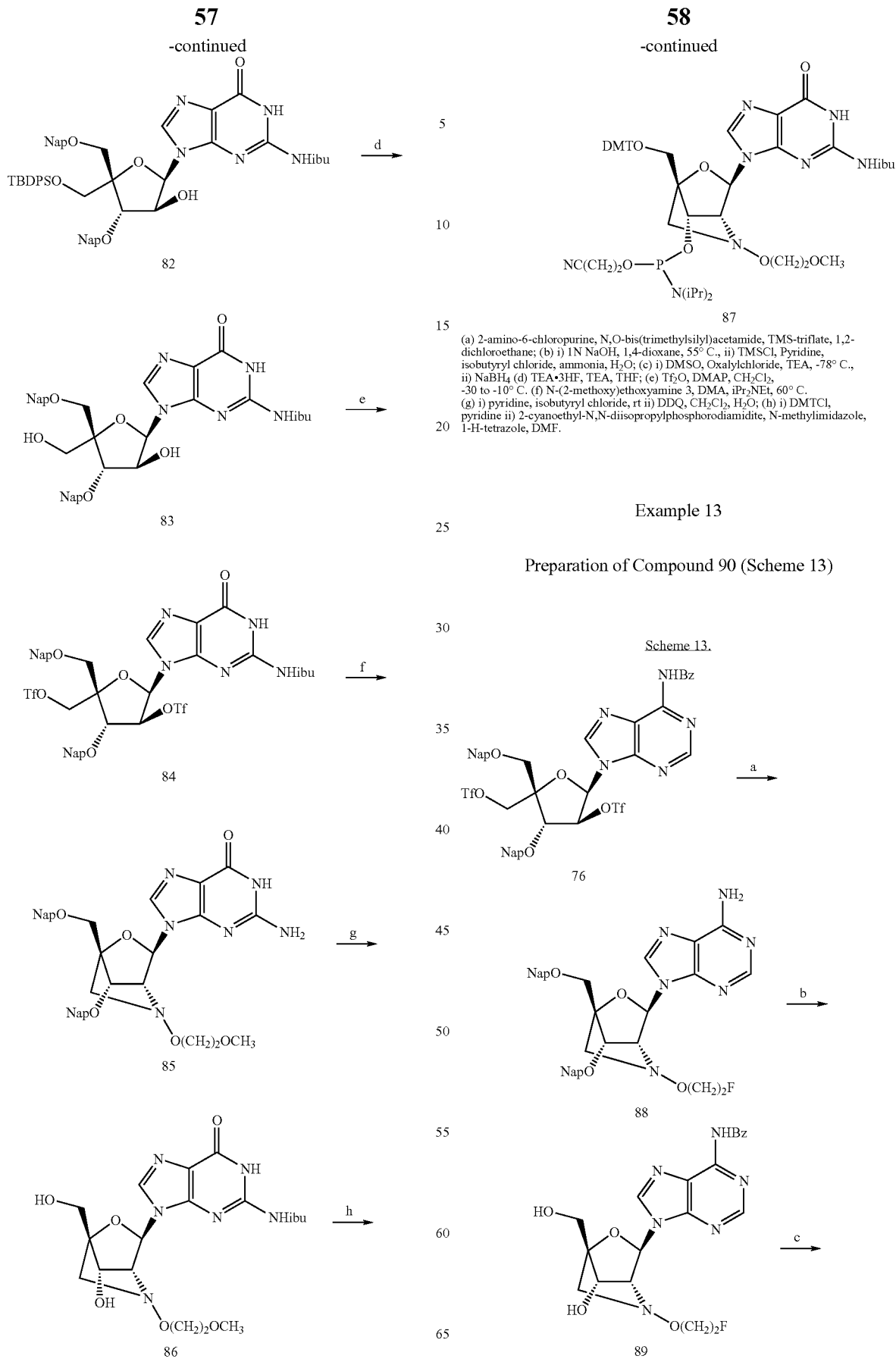

(a) 2-amino-6-chloropurine, N,O-bis(trimethylsilyl)acetamide, TMS-triflate, 1,2-dichloroethane; (b) i) 1N NaOH, 1,4-dioxane, 55° C., ii) TMSCl, Pyridine, isobutyryl chloride, ammonia, H₂O; (c) i) DMSO, Oxalylchloride, TEA, -78° C., ii) NaBH₄ (d) TEA•3HF, TEA, THF; (e) Tf₂O, DMAP, CH₂Cl₂, -30 to -10° C. (f) N-(2-methoxy)ethoxyamine 3, DMA, iPr₂NEt, 60° C. (g) i) pyridine, isobutyryl chloride, rt ii) DDQ, CH₂Cl₂, H₂O; (h) i) DMTCl, pyridine ii) 2-cyanoethyl-N,N-diisopropylphosphorodiamidite, N-methylimidazole, 1-H-tetrazole, DMF.

Example 13

Preparation of Compound 90 (Scheme 13)

Scheme 13.

59
-continued

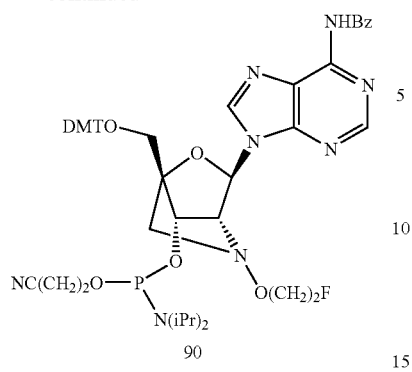

90

(a) N-(2-methoxy)ethoxyamine 16, DMA, iPr₂NEt, 60° C. (b) i) benzoyl tetrazole, DMF, 40° C.; ii) DDQ, CH₂Cl₂, H₂O; (c) i) DMTCl, pyridine, rt, ii) 2-cyanoethyl-N,N-diisopropylphosphorodiamidite, N-methylimidazole, 1-H-tetrazole, DMF.

60
-continued

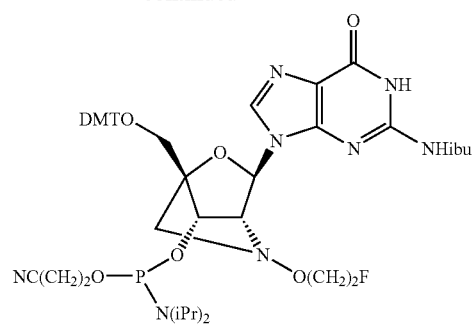

93

(a) N-2-(Fluoro)ethoxyamine 16, DMA, iPr₂NEt, 60° C.
(b) i) Pyridine, isobutyryl chloride, rt;
   ii) DDQ, CH₂Cl₂, H₂O;
(c) i) DMTCl, pyridine,
   ii) 2-cyanoethyl-N,N-diisopropylphosphorodiamidite, N-methylimidazole, 1-H-tetrazole, DMF.

Example 14

Preparation of Compound 93 (Scheme 14)

Scheme 14.

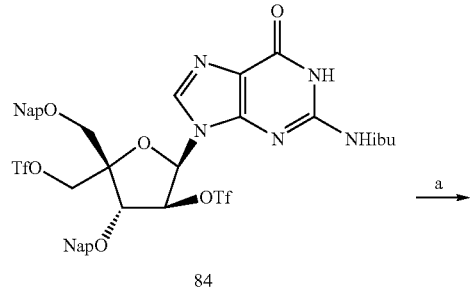

84

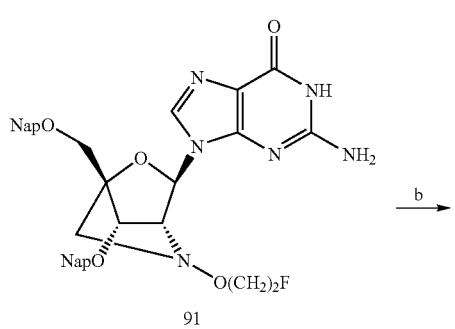

91

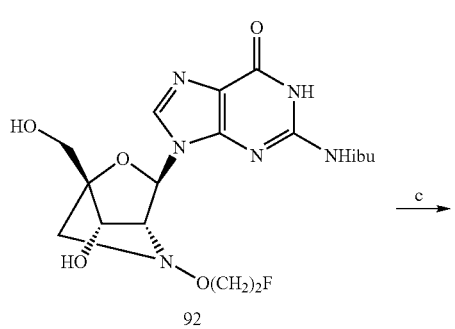

92

Example 15

Preparation of Compound 100 (Scheme 15)

Scheme 15.

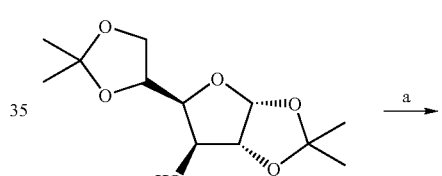

94

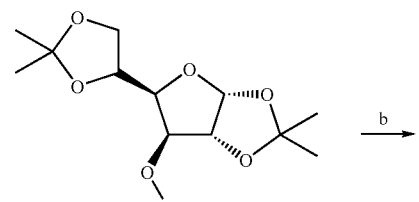

95

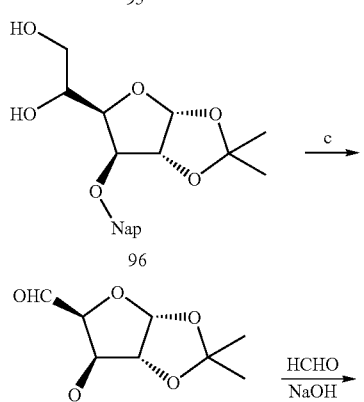

96

97

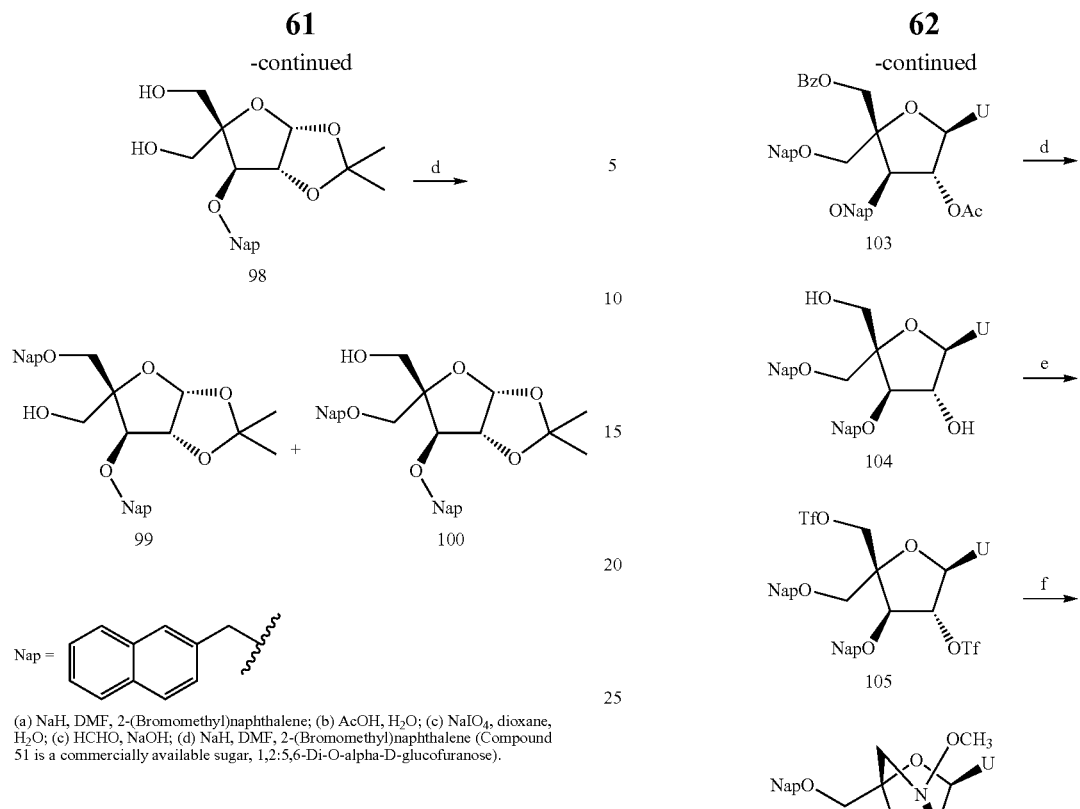

(a) NaH, DMF, 2-(Bromomethyl)naphthalene; (b) AcOH, H₂O; (c) NaIO₄, dioxane, H₂O; (c) HCHO, NaOH; (d) NaH, DMF, 2-(Bromomethyl)naphthalene (Compound 51 is a commercially available sugar, 1,2:5,6-Di-O-alpha-D-glucofuranose).

Example 16

Preparation of Compound 109 (Scheme 16)

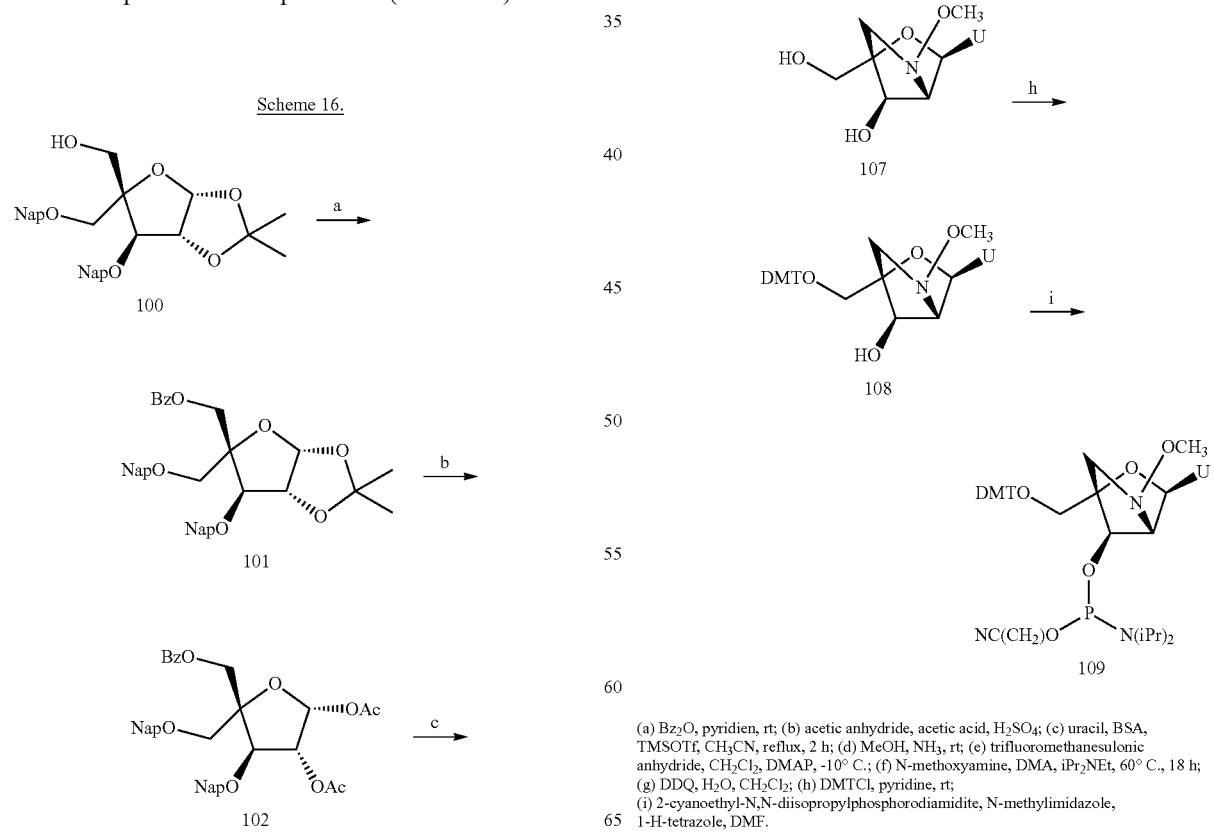

(a) Bz₂O, pyridien, rt; (b) acetic anhydride, acetic acid, H₂SO₄; (c) uracil, BSA, TMSOTf, CH₃CN, reflux, 2 h; (d) MeOH, NH₃, rt; (e) trifluoromethanesulonic anhydride, CH₂Cl₂, DMAP, -10° C.; (f) N-methoxyamine, DMA, iPr₂NEt, 60° C., 18 h; (g) DDQ, H₂O, CH₂Cl₂; (h) DMTCl, pyridine, rt; (i) 2-cyanoethyl-N,N-diisopropylphosphorodiamidite, N-methylimidazole, 1-H-tetrazole, DMF.

Example 17

Preparation of Compound 114 (Scheme 17)

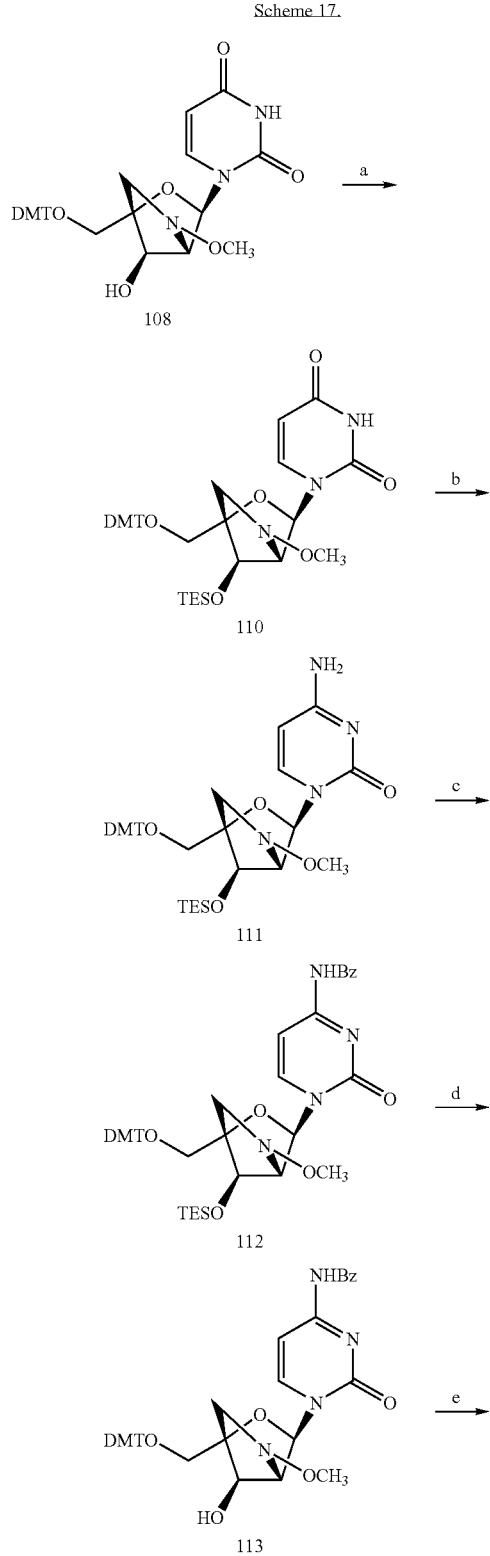

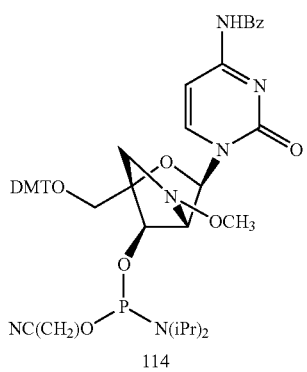

(a) DMF, imidazole, triethylsilyl chloride, rt; (b) i) 1,2,4-triazole, POCl$_3$, triethylamine, CH$_3$CN, 0° C. to rt, ii) aqueous NH$_3$, dioxane; (c) benzoic anhydride, DMF, rt; (d) triethylamine, triethylamine trihydrofluoride, THF, rt; (e) 2-cyanoethyl-N,N-diisopropylphosphorodimidite, N-methylimidazole, 1-H-tetrazole, DMF.

Example 18

Preparation of Compound 122 (Scheme 18)

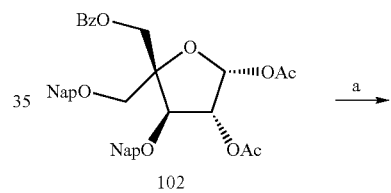

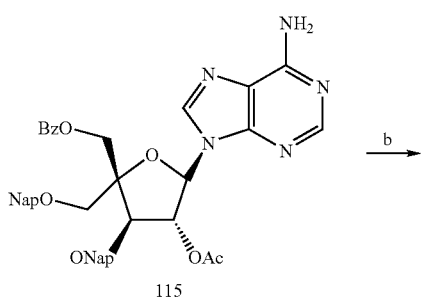

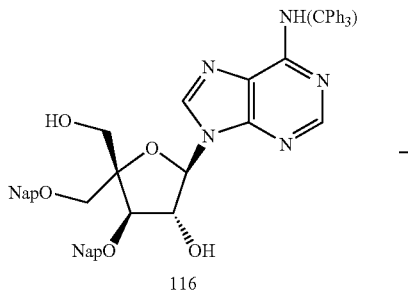

-continued

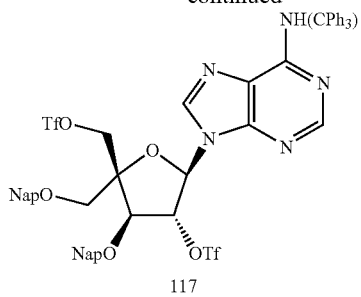
117

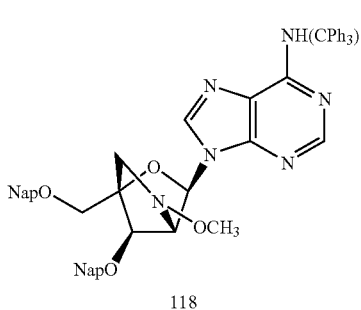
118

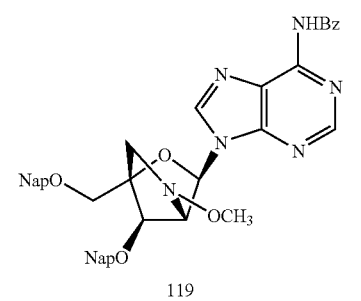
119

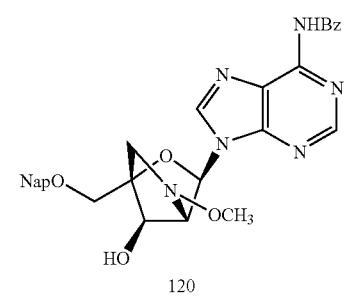
120

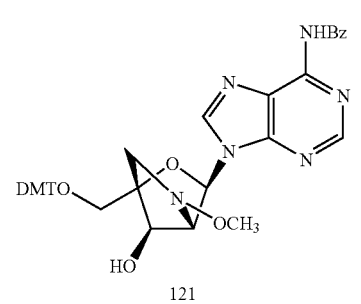
121

-continued

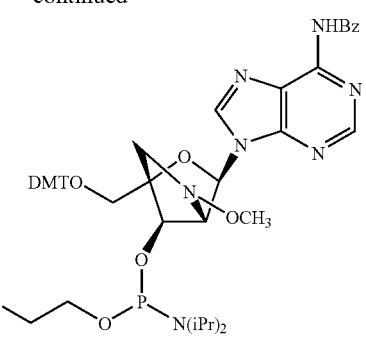
122

(a) adenine, SnCl₄, CH₃CN, rt;; (b) i) trityl chloride pyridine, 100° C., ii) MeOH, NH₃, rt; (c) trifluoromethanesulfonic anhydride, CH₂Cl₂, DMAP, -10° C.; (f) N-methoxyamine, DMA, iPr₂NEt, 60° C., 18 h; (e) i) 3% Dichloroactic acid in CH₂Cl₂, ii) benzoyl tetrazole, DMF, 40° C., iii) DDQ, H₂O, CH₂Cl₂; (g) DMTCl, pyridine, rt; (h) 2-cyanoethyl-N,N-diisopropylphosphorodiamidite, N-methylimidazole, 1-H-tetrazole, DMF.

Example 19

Preparation of Compound 129 (Scheme 19)

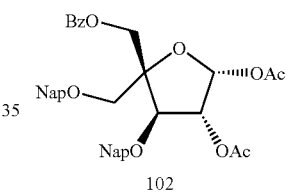

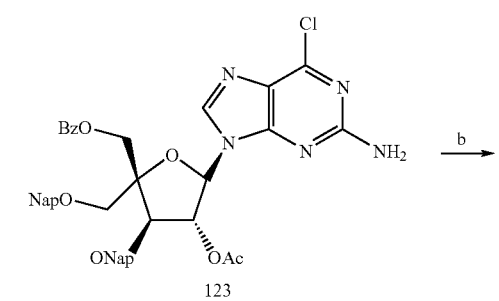
123

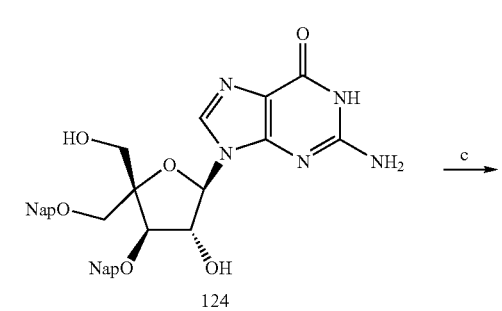
124

-continued

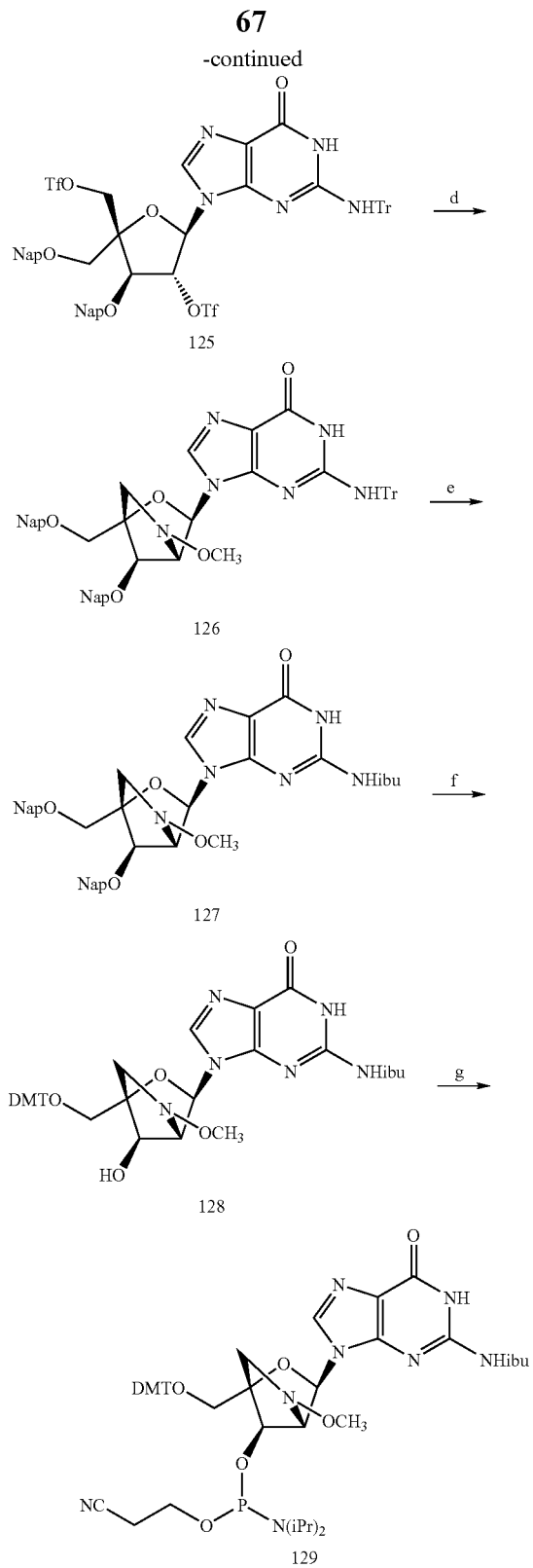

(a) 2-amino-6-chloropurine, N,O-bis(trimethylsilyl)acetamide, TMS-triflate, 1,2-dichloroethane; (b) aqueous NaOH, dioxane; (c) i) triethylsilylchloride, DMF, imidazole, ii) trityl chloride, DMAP, triethylamine, DMF, ii)
TEA•3HF, TE, THF, rt, iii) trifluoromethane-
sulonic anhydride, pyridine, 0° C.; (d) N-methoxyamine,
DMA, iPr₂NEt, 60° C., 18 h; (e) i) 3% dichloroactic acid in CH₂Cl₂, ii)
isobutyryl chloride, pyridine, rt; (f) i) DDQ, H₂O, CH₂Cl₂, ii) DMTCl, pyridine, rt;
(g) 2-cyanoethyl-N,N-diisopropylphosphorodiamidite, N-methylimidazole,
1-H-tetrazole, DMF, rt.

Example 20

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 21

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 0.2 M solution of phenylacetyl disulfide in 50% 3-picoline in acetonitrile for the oxidation of the phosphite linkages. The thiation reaction step time is increased to 180 see and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH₄OAc solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825; 5,386,023; 5,489,677; 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Example 22

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al, J. Biol. Chem. 1991, 266, 18162-18171, Results obtained with HPLC-purified material are generally similar to those obtained with non-HPLC purified material.

Example 23

Oligonucleotide Synthesis—96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 24

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 25

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

B.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 26

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of Monoclonal Antibodies is Taught in, for Example, Ausubel, F. M. et al., *Current Protocols in Molecular Biology*, Volume 2, pp. 11.4.1-1.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 27

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 28

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and butters purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 µL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 29

Real-Time Quantitative PCR Analysis of Target mRNA Levels

Quantitation of a target mRNA levels was accomplished by real-time quantitative PCR using the ABI PRISM™7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 µL PCR cocktail (2.5×PCR buffer minus $MgCl_2$, 6.6 mM $MgCl_2$. 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 30

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 01).

```
                                      (SEQ ID NO: 02)
Forward primer: AATGGCTAAGTGAAGATGACAATCAT (SEQ ID NO: 03)
Reverse primer: TGCACATATCATTACACCAGTTCGT
```

And the PCR probe:
FAM-TTGCAGCAATTCACTGTAAAGCTG-GAAAGG-TAMRA (SEQ ID NO: 04), where FAM is the fluorescent dye and TAMRA is the quencher dye.

Example 31

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 32

Effects of Antisense Compounds Targeting PTEN In Vitro Study

In certain embodiments, oligomeric compounds were synthesized and tested for their ability to reduce PTEN expression over a range of doses. B.END cells were treated with the N-methoxyl amino BNA (403045), 4'-$CH_2$—O-2' BNA (392745 and 392063) and 2'-MOE (392753) modified oligomers at concentrations of 0.625, 1.25, 2.5, 5, 10, 20 or 40 nM using methods described herein. Expression levels of PTEN were determined using real-time PCR and normalized to RIBOGREEN™ as described in other examples herein. The percent inhibition of PTEN mRNA was determined. Resulting dose-response curves were used to determine the $IC_{50}$ and Tm's were assessed in 100 mM phosphate buffer; 0.1 mM EDTA, pH 7, at 260 nm using 4 μM modified oligomers and 4 μM complementary length matched RNA. The activities are listed below.

| SEQ ID NO/ISIS NO | Composition (5' to 3') |
|---|---|
| 05/403045 | $C_nU_n$TAGCACTGGCC$_nU_n$ |
| 05/392745 | $C_1U_1$TAGCACTGGCC$_1U_1$ |
| 05/392063 | $^{Me}C_1T_1$TAGCACTGGC$^{Me}C_1T_1$ |
| 05/392753 | $C_eU_e$TAGCACTGGCC$_eU_e$ |

Each internucleoside linking group is a phosphorothioate; subscript n indicates that the preceding nucleoside is an N-methoxy-amino bicyclic nucleoside; subscript 1 indicates that the preceding nucleoside is a bicyclic nucleoside having a 4'-$CH_2$—O-2' bridge; subscript e indicates that the preceding nucleoside is a 2'-$(CH_2)_2OCH_3$(MOE) modified nucleoside; superscript Me indicates that the following nucleoside is a 5-methyl-base modified nucleoside; and each nucleoside not otherwise annotated is a 2'-deoxyribonucleoside.

| SEQ ID NO/ISIS NO | % Inhibition of PTEN mRNA @ Dose | | | | |
|---|---|---|---|---|---|
| | 0.625 nM | 1.25 nM | 2.5 nM | 5 nM | 10 nM |
| 05/392063 | 0 | 34 | 55 | 65 | 84 |
| 05/392745 | 10 | 40 | 59 | 71 | 85 |
| 05/392753 | 0 | 0 | 8 | 22 | 50 |
| 05/403045 | 4 | 31 | 55 | 71 | 80 |

| SEQ ID NO/ISIS NO | 20 nM | 40 nM | $IC_{50}$ | Tm ° C. |
|---|---|---|---|---|
| 05/392063 | 88 | 92 | 2.7 | 60.6 |
| 05/392745 | 92 | 93 | 2.1 | 58.9 |
| 05/392753 | 67 | 84 | 11.6 | 51.3 |
| 05/403045 | 80 | 92 | 2.7 | 57.7 |

Example 33

Effects of Antisense Compounds Targeting PTEN In Vivo Study

Six week old male Balb/c mice (Jackson Laboratory, Bar Harbor, Me.) were injected twice weekly for 3 weeks with N-methoxyl-amino-BNA (403045), and 4'-$CH_2$—O-2' BNA (392063) modified oligomers targeted to PTEN at a dose of 3.2, 1.0, 0.32 or 0.1 μmol/kg. The mice were sacrificed 48 hours following the final administration. Liver tissues were homogenized and PTEN mRNA levels were quantitated using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. The table below shows comparisons of the antisense compounds targeting PTEN nucleic acid for their effect on target mRNA reduction. Results are presented as the average % inhibition of mRNA expression for each antisense compound, normalized to saline-injected control.

| SEQ ID NO/ISIS NO | Composition (5' to 3') | % Inhibition of PTEN mRNA @ Dose (μmol/kg) | | | |
|---|---|---|---|---|---|
| | | 0.1 | 0.32 | 1.0 | 3.2 |
| 05/403045 | $C_nU_n$TAGCACTGGCC$_nU_n$ | 0 | 2 | 29 | 75 |
| 05/392063 | $^{Me}C_1T_1$TAGCACTGGC$^{Me}C_1T_1$ | 4 | 16 | 70 | 93 |

Each internucleoside linking group is a phosphorothioate; subscript n indicates that the preceding nucleoside is an N-methoxy-amino bicyclic nucleoside; subscript 1 indicates that the preceding nucleoside is a bicyclic nucleoside having a 4'-$CH_2$—O-2' bridge; superscript Me indicates that the following nucleoside is a 5-methyl-base modified nucleoside; and each nucleoside not otherwise annotated is a 2'-deoxyribonucleoside.

As shown above, each antisense compound demonstrated a dose-dependent reduction in PTEN mRNA levels. The results demonstrate that N-methoxy amino BNA gapmer 403045 is about 2.5 told less active than 4'-$CH_2$—O-2' BNA gapmer 392063.

The $ED_{50}$ for 403045 and 392063 were determined by comparing oligonucleotide concentration in the liver to inhibition of PTEN mRNA. Antisense oligomers 403045 and 392063 were found to exhibit an $ED_{50}$ of 7.9 mg/kg (1.71 µmol/kg) and 3.1 mg/kg (0.68 µmol/kg) respectively. $ED_{50}$ is defined as the effective dose required displaying 50% of reduction in PTEN mRNA.

Liver transaminase levels, alanine aminotranfereese (ALT) and aspartate aminotransferase (AST), in serum were measured relative to saline injected mice. The approximate liver transaminase levels are listed in the table below.

| SEQ ID NO/ISIS NO | Dose (µmol/kg) | ALT (IU/L) | AST (IU/L) |
|---|---|---|---|
| Saline N/A | 24.8 | 62 | |
| 05/403045 | 0.1 | 30.8 | 85.8 |
| | 0.32 | 21.3 | 62.5 |
| | 1 | 17 | 55.8 |
| | 3.2 | 16.5 | 60.3 |
| 05/392063 | 0.1 | 23.8 | 53 |
| | 0.32 | 27.8 | 110.5 |
| | 1 | 38.5 | 80 |
| | 3.2 | 321.8 | 265.8 |

A slight decrease in total body weights was observed in mice treated with 392063 as compared to mice treated with saline alone. There is no significant change in total body weights for mice treated with 403045 as compared to the total body weights of mice treated with saline alone.

Example 34

Effects of Antisense Compounds Targeting PTEN In Vivo Study

Six week old male Balb/c mice (Jackson Laboratory, Bar Harbor, Me.) were injected once with 2'-MOE (394424), 4'-CH$_2$—O-2' BNA (392056), and N-methoxylamino (403747) modified oligomers targeted to PTEN at a dose of 2.5, 5, 10, or 20 µmol/kg. The mice were sacrificed 72 hours following the final administration. Liver tissues were homogenized and PTEN mRNA levels were quantitated using real-time PCR and RIBOGREEN™ RNA quantification reagent (Molecular Probes, Inc Eugene, Oreg.) according to standard protocols. PTEN mRNA levels were determined relative to total RNA (using Ribogreen), prior to normalization to saline-treated control. The relative activities of the antisense compounds are shown below with the results presented as the average inhibition of mRNA expression for each antisense compound, normalized to saline-injected control.

| SEQ ID NO/ ISIS NO | Sequence | PTEN % Inhibition (µmol/kg dose) | | | |
|---|---|---|---|---|---|
| | | 2.5 | 5.0 | 10 | 20 |
| 06/394424 | T$_e$$^{Me}$C$_e$ATGGCTGCAG$^{Me}$C$_e$T$_e$ | n/a | n/a | n/a | 29 |
| 06/392056 | T$_1$$^{Me}$C$_1$ATGGCTGCAG$^{Me}$C$_1$T$_1$ | 42 | 61 | 82 | n/a 60 |
| 07/403747 | U$_n$C$_n$ATGGCTGCAGC$_n$U$_n$ | 34 | 52 | 68 | 79 |

Each internucleoside linking group is a phosphorothioate; subscript n indicates that the preceding nucleoside is an N-methoxy-amino bicyclic nucleoside; subscript 1 indicates that the preceding nucleoside is a bicyclic nucleoside having a 4'-CH$_2$—O-2' bridge; subscript e indicates that the preceding nucleoside is a 2'-(CH$_2$)$_2$OCH$_3$ (MOE) modified nucleoside; superscript Me indicates that the following nucleoside is a 5-methyl-base modified nucleoside; and each nucleoside not otherwise annotated is a 2'-deoxyribonucleoside.

In certain embodiments, ALT and AST levels were measured in mice treated with the antisense oligomers 394424, 392056, and 403747. Serum was analyzed by LabCorp Testing Facility (San Diego, Calif.) and ALT and AST levels in serum were measured relative to saline injected mice. The approximate ALT and AST levels are listed in the table below.

| SEQ ID NO/ISIS NO | Dose (µmol/kg) | ALT (IU/L) | AST (IU/L) |
|---|---|---|---|
| Saline | N/A | 33 | 70 |
| 06/394424 | 20 | 26 | 49 |
| 06/392056 | 2.5 | 39 | 62 |
| | 5 | 319 | 181 |
| | 10 | 890 | 593 |
| 07/403747 | 2.5 | 31 | 65 |
| | 5 | 37 | 55 |
| | 10 | 91 | 84 |
| | 20 | 348 | 281. |

Example 35

Nuclease Stability, Snake Venom Phosphodiesterase Treatment

The nuclease stability of a DNA oligomer compared with modified oligomers having N-methoxyamino BNA, 4'-CH$_2$—O-2' BNA and 2'-MOE modified nucleosides were determined following treatment with snake venom phosphodiesterase (SVPD). Each of the test oligomers was incubated with SVPD (0.0005 U/mL) in 50 mM Tris-HCl, pH 7.5, 8 mM MgCl$_2$ at 37° C. to a final concentration of 5 µM in a total volume of 100-150 µL. At each time point, a 10 µL aliquot and quenching buffer (8 M Urea, 50 mM EDTA) was placed in a 500 µL microfuge tube. Kinetic time points were taken at 0, 1, 2, and 4 minutes for 7153; 0, 5, 10, and 15 minutes for 395421 and 395423; and 0, 30, 60, 120, 240 and 480 minutes for 403872. The samples were then cooled on ice and spun in a Microfuge to bring the entire volume to the bottom of the tube. Samples were kept frozen until ready for LC/MS analysis.

For each sample the oligomer and metabolites were separated and analyzed using IP-HPLC/MS techniques. Samples were diluted to a concentration of 1 µM with quenching buffer in a microsampling vial and 50 µL of the sample was injected into the IP-HPLC column (YMC ODS-AQ™ 1.0 mm×150 mm, 3 µm, 120 A°). The loading buffer used was 25 mM TBAA (tributyl ammonium acetate) in 25% acetonitrile. The mobile phase "A" was 5 mM TBAA in 20% acetonitrile and the mobile phase "B" was 5 mM TBAA in 90% acetonitrile. Conditions: 0-4 min 10% B, 4-26 min 65% B, 26-32 min 75% B; flow 0.1 mL min$^{-1}$; wave length 260 nm. The percentages of the full-length oligomers were calculated by integration using Caesar v. 6 software (Senetec Software, New Jersey) and the oligonucleotide half-lives were calculated using GraphPad Prism 4.

| SEQ ID NO./ ISIS NO. | Composition (5' to 3') | modification | Half Life (min) |
|---|---|---|---|
| 08/7157 | TTTTTTTTTTTT | unmodified (2'-H), DNA | 0.6 |
| 08/395421 | TTTTTTTTTT$_e$T$_e$ | 2'-MOE | 3.4 |
| 09/395423 | TTTTTTTTTTU$_1$U$_1$ | 4'-CH$_2$—O-2' BNA | 5.0 |
| 09/403872 | TTTTTTTTTTU$_n$U$_n$ | N-Methoxyamino BNA | 188.0 |

Each internucleoside linking group is a phosphorothioate; subscript n indicates that the preceding nucleoside is an N-methoxy-amino bicyclic nucleoside; subscript 1 indicates that the preceding nucleoside is a bicyclic nucleoside having a 4'-CH$_2$—O-2' bridge; subscript e indicates that the preceding nucleoside is a 2'-(CH$_2$)$_2$OCH$_3$ (MOE) modified nucleoside; and each nucleoside not otherwise annotated is a 2'-deoxyribonucleoside.

As shown, the half life of N-methoxyamino BNA modified oligomer (403872) was increased compared to the half lives calculated for the 2'-MOE (395423) and 4'-CH$_2$—O-2' BNA (395421) modified oligomers.

All publications, patents, and patent applications referenced herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A bicyclic nucleoside having Formula I:

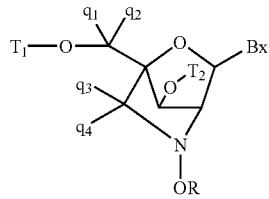

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

R is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

2. The bicyclic nucleoside of claim 1 wherein R is $C_1$-$C_6$ alkyl or substituted $C_1$-$C_6$ alkyl.

3. The bicyclic nucleoside of claim 2 wherein R is methyl, —(CH$_2$)$_2$OCH$_3$ or —(CH$_2$)$_2$F.

4. The bicyclic nucleoside of claim 1 having Formula I and further having the configuration of Formula Ia:

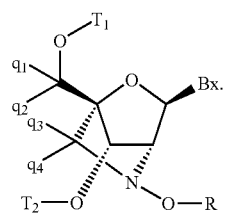

5. The bicyclic nucleoside of claim 1 having Formula I and further having the configuration of Formula Ib:

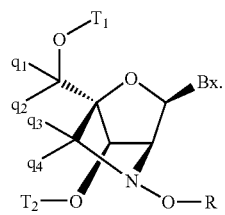

6. The bicyclic nucleoside of claim 1 wherein one of $q_1$, $q_2$, $q_3$ and $q_4$ is $CH_3$ and the other three of $q_1$, $q_2$, $q_3$ and $q_4$ are independently H.

7. The bicyclic nucleoside of claim 1 wherein one of $q_1$ and $q_2$ is $CH_3$ and one of $q_3$ and $q_4$ is $CH_3$ and the other two of $q_1$, $q_2$, $q_3$ and $q_4$ are independently H.

8. The bicyclic nucleoside of claim 1 wherein $T_1$ is H or 4,4'-dimethoxy-trityl and $T_2$ is H, diisopropylcyanoethoxy phosphoramidite or H-phosphonate.

9. The bicyclic nucleoside of claim 1 wherein $T_1$ is 4,4'-dimethoxytrityl and $T_2$ is diisopropylcyanoethoxy phosphoramidite.

10. The bicyclic nucleoside claim 1 wherein Bx is uracil, thymine, cytosine, 5-methylcytosine, 5-thiazolo-uracil, 5-thiazolo-cytosine, adenine, guanine, 2,6-diaminopurine, or other substituted or unsubstituted purine or pyrimidine.

11. An oligomeric compound comprising at least one bicyclic nucleoside having Formula II:

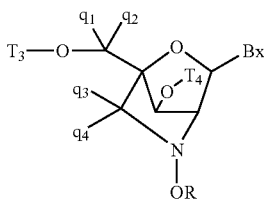

wherein independently for each of said at least one bicyclic nucleoside having Formula II:

Bx is a heterocyclic base moiety;

$T_3$ and $T_4$ are each, independently, an internucleoside linking group linking the bicyclic nucleoside to the oligomeric compound or one of $T_3$ and $T_4$ is an internucleoside linking group linking the bicyclic nucleoside to the oligomeric compound and the other of $T_3$ and $T_4$ is H, a hydroxyl protecting group, a linked conjugate group or a 5' or 3'-terminal group;

R is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$q_3$ and $q_4$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

wherein each substituted group is, independently, mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

12. The oligomeric compound of claim 11 wherein for each bicyclic nucleoside having Formula II R is $C_1$-$C_6$ alkyl or substituted $C_1$-$C_6$ alkyl.

13. The oligomeric compound of claim 11 wherein for each bicyclic nucleoside having Formula II R is methyl, —(CH$_2$)$_2$OCH$_3$ or —(CH$_2$)$_2$F.

14. The oligomeric compound of claim 11 wherein each bicyclic nucleoside having Formula II has the configuration of Formula IIa:

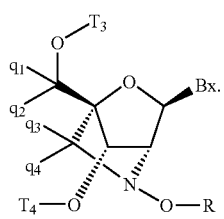

15. The oligomeric compound of claim 11 wherein each bicyclic nucleoside having Formula II has the configuration of Formula IIb:

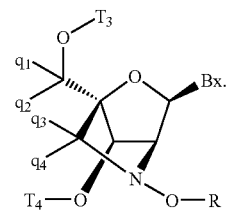

16. The oligomeric compound of claim 11 wherein independently for each bicyclic nucleoside having Formula II one of $q_1$, $q_2$, $q_3$ and $q_4$ is CH$_3$ and the other three of $q_1$, $q_2$, $q_3$ and $q_4$ are independently H.

17. The oligomeric compound of claim 11 wherein independently for each bicyclic nucleoside having Formula II one of $q_1$ and $q_2$ is CH$_3$ and one of $q_3$ and $q_4$ is CH$_3$ and the other two of $q_1$, $q_2$, $q_3$ and $q_4$ are independently H.

18. The oligomeric compound of claim 11 wherein each internucleoside linking group is, independently, a phosphodiester or a phosphorothioate.

19. The oligomeric compound of claim 11 comprising at least one region of at least two contiguous bicyclic nucleosides having Formula II located at either the 3' or the 5'-end of the oligomeric compound.

20. The oligomeric compound of claim 11 comprising gapped oligomeric compound having at least two regions, each region comprising from 1 to about 5 contiguous bicyclic nucleosides having Formula II, wherein one of said regions of bicyclic nucleosides having Formula II is located externally at the 5'-end and the other of said regions is located externally at the 3'-end and wherein the two external regions are separated by an internal region comprising from about 6 to about 14 monomeric subunits independently selected from nucleosides and modified nucleosides.

21. The oligomeric compound of claim 11 comprising from about 8 to about 40 monomers in length.

22. The oligomeric compound of claim 11 comprising from about 12 to about 16 monomers in length.

23. A method of inhibiting gene expression comprising contacting a cell with an oligomeric compound comprising at least one bicyclic nucleoside of claim 11 and wherein said oligomeric compound comprises from about 8 to about 40 monomeric subunits and is complementary to a target RNA.

24. The method of claim 23 wherein said cell is in an animal.

25. The method of claim 23 wherein said cell is in a human.

26. The method of claim 23 wherein said target RNA is selected from mRNA, pre-mRNA and micro RNA.

27. The method of claim 23 wherein said target RNA is mRNA.

28. The method of claim 23 wherein said target RNA is human mRNA.

29. The method of claim 23 wherein said target RNA is cleaved thereby inhibiting its function.

30. The method of claim 23 further comprising detecting the levels of target RNA.

\* \* \* \* \*